US008372963B2

United States Patent
Grunwald et al.

(10) Patent No.: US 8,372,963 B2
(45) Date of Patent: Feb. 12, 2013

(54) RSV F-PROTEIN AND ITS USE

(75) Inventors: Thomas Grunwald, Bochum (DE); Klaus Ueberla, Sprockhoevel (DE)

(73) Assignees: Pevion Biotech AG (CH); Ruhr-Universitaet Bochum (DE)

(*) Notice: Subject to any disclaimer, the term of this patent is extended or adjusted under 35 U.S.C. 154(b) by 615 days.

(21) Appl. No.: 12/520,321

(22) PCT Filed: Dec. 18, 2007

(86) PCT No.: PCT/EP2007/011090
§ 371 (c)(1), (2), (4) Date: Dec. 14, 2009

(87) PCT Pub. No.: WO2008/077527
PCT Pub. Date: Jul. 3, 2008

(65) Prior Publication Data
US 2010/0111989 A1    May 6, 2010

(30) Foreign Application Priority Data
Dec. 21, 2006 (DE) .......................... 10 2006 060 799

(51) Int. Cl.
| C07H 21/02 | (2006.01) |
| C07H 21/04 | (2006.01) |
| C07K 1/00 | (2006.01) |
| C07K 14/00 | (2006.01) |
| C07K 17/00 | (2006.01) |
| A61K 39/00 | (2006.01) |
| A61K 39/38 | (2006.01) |
| A61K 39/12 | (2006.01) |
| A61K 39/155 | (2006.01) |

(52) U.S. Cl. .................. 536/23.72; 536/23.1; 536/23.7; 530/350; 424/184.1; 424/186.1; 424/204.1; 424/211.1; 435/69.1; 435/320.1

(58) Field of Classification Search .................. None
See application file for complete search history.

(56) References Cited

U.S. PATENT DOCUMENTS
| 5,716,823 A | 2/1998 | Wertz et al. |
| 5,922,576 A | 7/1999 | He et al. |
| 6,083,925 A | 7/2000 | Li et al. |

FOREIGN PATENT DOCUMENTS
| WO | WO 93/14207 | 7/1993 |
| WO | WO 00/18929 A2 | 4/2000 |
| WO | WO 00/18929 A3 | 4/2000 |
| WO | WO 2006/050280 | 5/2006 |

OTHER PUBLICATIONS

Hsu et al. Immunogenicity of Recombinant Adenovirus-Respiratory Syncytial Virus Vaccines with Adenovirus Types 4, 5, and 7 Vectors in Dogs and a Chimpanzee. The Journal of Infectious Diseases 1992, vol. 166, pp. 769-775.*
Murphy et al. Adenovirus EIIA early promoter: Transcriptional control elements and induction by the viral pre-early EIA gene. Proceedings of the National Academy of Sciences of the United States of America, Apr. 1985, vol. 82, pp. 2230-2234.*
Du, et al., "A Prototype Recombinant Vaccine Against Respiratory Syncytial Virus and Parainfluenza Virus Type 3," 1994, *Bio/Technology*, 12:813-818.
Tang, et al., "Parainfluenza Virus Type 3 Expressing the Native or Soluble Fusion (F) Protein of Respiratory Syncytial Virus (RSV) Confers Protection from RSV Infection in African Green Monkeys," 2004, *Journal of Virology*, 78(20):11198-11207.
Branigan, et al., 2005, Virology Journal (BIOMED Central, London GB) 2(1):1-12, "Use of a Novel Cell-Based Fusion Reporter Assay to Explore the Host Range of Human Respiratory Syncytial Virus F Protein".
Park, et al., 2001, Molecules and Cells 12(1):50-56, "Immune Induction and Modulation in Mice Following Immunization with DNA Encoding F Protein of Respiratory Syncytial Virus".
Li, et al., 1998, Journal of Experimental Medicine (Tokyo, JP) 188(4):681-688, "Protection Against Respiratory Syncytial Virus Infection by DNA Immunization".
Tree, et al., 2004, Vaccine, Butterworth Scientific. (Guildford, GB) 22(19):2438-2443, "An Assessment of Different DNA Delivery systems for Protection Against Respiratory Syncytial Virus Infection in Murine Model:Gene-Gun Delivery Induces IgG in the Lung".
Ternette et al., 2007, Vaccine, Butterworth Scientific. (Guildford, GB) 25(41):7271-7279, "Immunogenicity and Efficacy of Codon Optimized DNA Vaccines encoding the F-protein of Respiratory Syncytial Virus".
Grunwald, et al., 2008, BIOVARIA (http://www.biovaris.net/downloads/BioVaris_Us.pdf) Abstract, "RSV-vaccine:Vaccine Based on Adenoviral Vectors Preventing Infection with the Respiratory Syncytial Virus".
DuBridge, et al., 1987, Molecular and Callular Biology, 7(1):379-387, "Analysis of Mutation in Human Cells by Using an Epstein-Barr Virus Shuttle System".

* cited by examiner

*Primary Examiner* — Louise Humphrey
(74) *Attorney, Agent, or Firm* — Riverside Law LLP

(57) ABSTRACT

The present invention relates to a nucleic acid molecule, which codes for the F-protein of the respiratory syncytial virus (RSV) or a fragment thereof, for the expression in a human cell environment of codon optimized variants of said nucleic acid molecule, vectors and compositions comprising said nucleic acid molecules and the use thereof as vaccines and polypeptides coded by the nucleic acid molecules and method for the production thereof.

16 Claims, 15 Drawing Sheets

Figure 15

RSV F-PROTEIN AND ITS USE

REFERENCE TO RELATED APPLICATIONS

This is a National Stage application of PCT International Application No. PCT/EP2007/011090, filed Dec. 18, 2007, which in turn claims the benefit of DE Application No. 102006060799.6 filed on Dec. 21, 2006, which is hereby incorporated by reference in its entirety herein.

FIELD OF THE INVENTION

The present invention is directed to a nucleic acid molecule which codes for the F-protein of the respiratory syncytial virus or a fragment thereof, for the expression in a human cell environment, codon-optimized variants of this nucleic acid molecule and their use with viral vectors or plasmid vectors as vaccines.

BACKGROUND OF THE INVENTION

As early as 1957 a virus was identified in children with severe diseases of the lower airway, which was designated respiratory syncytial virus (RSV). This name refers to the characteristic of the virus to cause diseases of the respiratory tract and to induce the formation of synctia in vitro.

RSV belongs to the family of paramyxoviruses and, within this, to the subfamily of the pneumoviriane. As with the other representatives of this family, RSV has a non-segmented, continuous RNA genome in negative strand orientation. The genome of the RSV is 15222 bases long and exists in complex with proteins as a nucleocapsid.

The virus genome codes a series of virus proteins. Among these are the membrane proteins, which are known as RSV G-proteins and RSV F-proteins. The G-proteins is responsible for the specific adsorption of the virus particle onto the cell surface, while the F-protein induces the fusion of the viral with the cellular membrane. The F-protein is synthesized as a precursor polypeptide $F_0$ and has on the N-terminal end, a signal peptide for the transport of the translocation complex to the membrane of the endoplasmic reticulum. After the amino acid chain is fed through the membrane, a hydrophobic sequence at the C-terminal end effects the anchoring of the $F_0$ protein in the membrane and the signal peptide is cleaved off. Following this, the protein is glycosylated during its transport through the Golgi apparatus. A cleavage of the $F_0$ protein into the amino terminal $F_2$ part and the $F_1$ protein also takes place in the Golgi apparatus. The cleavage site lies between a segment of basic amino acids and a hydrophobic domain. This hydrophobic domain of about 25 amino acids in length forms, after the cleavage, the N-terminus of the $F_1$ protein and mediates the merging of the viral with the cellular membrane following absorption. The $F_2$ protein remains connected to the $F_1$ protein via a disulfide bridge.

Antibodies directed against this fusion-mediating peptide of the $F_1$ protein can prevent the virus from being taken up into the cell and thus have a neutralizing effect.

Infection with RSV is highly contagious; in a milliliter of saliva there exist up to $10^6$ infectious virus particles. It is transmitted primarily by droplet and direct contact with infected persons. Especially children become infected during the winter months.

RSV is considered the main infectological problem of the first year of life. Infants in the age between six weeks and a half year are especially in danger. At the age of four years, 80% of children have antibodies against the virus.

However, reinfections with mild forms of the disease also develop in later age as a result of a reduced antibody concentration. Especially frequent are noskomial infections in convalescent homes, kindergartens and -clinics.

The incubation time of RSV is approximately 4-5 days. The disease presents with mild to severe life threatening influenzal infections with fever and sniffles. Infections of the throat (pharyngitis) and the trachea (tracheitis) as well as of the bronchiae (bronchitis) are also commonly observed.

Following the droplet infection of the upper respiratory tract, the virus reproduces in the cells of the mucous membranes and, from there, can spread into the lower air passages within one to two days.

A vaccine against RSV is not presently known. Viruses killed by formalin were minimally successful, since the F-protein is destroyed by the chemical treatment and only antibodies against the G-protein are formed. While these are virus-neutralizing, they cannot however prevent the spread of the virus by cell fusions. Although a passive immunization by giving immunoglobulins is used, it is associated with high costs and is thus unsuitable for the prophylactic immunization of larger population groups.

There thus continues to exist a need for an effective vaccine against an infection with RSV.

SUMMARY OF THE INVENTION

The present invention is directed to a nucleic acid molecule, which comprises a nucleotide sequence which codes for the F-protein of the respiratory syncytial virus (RSV) or an immunogenic fragment thereof, as well as polynucleotides derived from this nucleic acid molecule which were codon-optimized for an efficient expression of the F-protein of RSV in a host cell. In one embodiment the nucleotide sequence which codes for an F-protein of RSV comprises the nucleotide sequence of SEQ ID NO: 1 or a fragment thereof. A nucleotide sequence which has been codon-optimized for the expression of the F-protein in a human host cell can, for example, comprise the nucleotide sequence of SEQ ID NO: 2 or a fragment thereof.

In one embodiment of the invention, the nucleotide sequence which codes for the F-protein of RSV consists of SEQ ID NO: 1 or a fragment thereof. In an alternative embodiment the nucleotide sequence which codes for the F protein of RSV consists of the nucleotide sequence of the codon-optimized nucleotide sequence SEQ ID NO: 2 or a fragment thereof.

A further aspect of this invention are the polypeptide molecules obtained by the expression of the nucleic acid molecules according to the invention. In one embodiment these polypeptides comprise or consist of the amino acid sequence SEQ ID NO: 3 or a fragment thereof.

The present invention also further comprises a vector which contains one of the nucleic acid molecules according to the invention. The nucleic acid molecules according to the invention can be contained in the vector in the form of an (expression) cassette which, in addition to the nucleotide sequence according to the invention, can also comprise a transcription- and/or translation control sequence, such as for example a promoter, functionally linked with the nucleic acid sequence. A still further aspect of this invention are cells which contain such a vector.

In a preferred embodiment of the invention the vector used is a viral vector or a plasmid. Especially preferred is an adenoviral vector, in which the E1-region is at least partially deleted, so that adenoviral vector is replication deficient. In addition the E3-region can also optionally be deleted.

In one embodiment of the invention the adenoviral vector contains the nucleotide sequence according to the invention in the form of an expression cassette in which the nucleotide sequence coding the F protein of RSV is functionally linked with a suitable promoter, for example the CMV promoter. The promoter used in the adenoviral vector is preferably regulable, for example a tetracycline regulable promoter, in order to prevent the expression of the F-protein in the adenoviral production cell. In all cells which do not contain the regulation system, the promoter is active and expresses the F-protein of RSV. Such an adenoviral vector can be employed as a vaccine vector.

In a further aspect the present invention also comprises plasmid vectors which comprise the nucleotide sequences according to the invention. In one embodiment these plasmid vectors can be employed as shuttle vectors and thus comprise a nucleic acid portion which enables homologous recombination with a suitable backbone plasmid, which for example contains a majority of a viral genome. It is especially preferred that adenoviral sequences are contained in the shuttle vector, said sequences allowing the homologous recombination with another plasmid which contains the majority of the adenoviral genome. In this way, the above-mentioned adenoviral vaccine vectors can for example be made.

In a further aspect the present invention further refers to immunogenic compositions which comprise the nucleotide sequences with SEQ ID NO: 1 or 2 or fragments thereof according to the invention. In one such composition, the nucleotide sequence according to the invention can also be present in the form of the above-mentioned vectors, preferably in the form of an adenoviral vaccine vector. One such vector allows the transport of the nucleic acid molecules according to the invention into a human host and the expression of the coded protein. Here, the protein is expressed in an amount which suffices to elicit the intended immune response.

Alternatively, the immunogenic compositions can also contain the proteins coded by these nucleotide sequences.

Depending on the desired type of use, the immunogenic compositions can also contain a pharmaceutically acceptable carrier and, if need be, further excipients.

A further aspect is the use of the nucleic acid molecules, vectors or proteins according to the invention of the preparation of a vaccine composition for the vaccination of a subject against diseases caused by infection with RSV. This subject is preferably a human.

The present invention further relates to a method for the preparation of the RSV F-protein, wherein the method comprises the expression of a nucleic acid molecule according to the invention in a suitable host cell. In a preferred embodiment of this method, the nucleic acid molecule according to the invention is codon-optimized for expression in the host cell.

BRIEF DESCRIPTION OF THE FIGURES

FIG. 15 shows an analysis of the expression strengths. The expression of the codon-optimized construct of the RSV-F protein with the upstream intron (plFsyn) was compared by serial dilution ($1:10^2$ to $1:10^4$) of the cell lysate with the expression of the plasmid with the wild-type sequence with the upstream intron (plFwt) in undiluted cell lysate (1:1). The amount of protein from RSV-F by expression of the codon-optimized construct at a dilution of 1000 fold ($1:10^3$) is significantly higher than that by the plasmid with the original sequence (kDa=molecular weight in kilodalton).

DETAILED DESCRIPTION OF THE INVENTION

Figure 1:
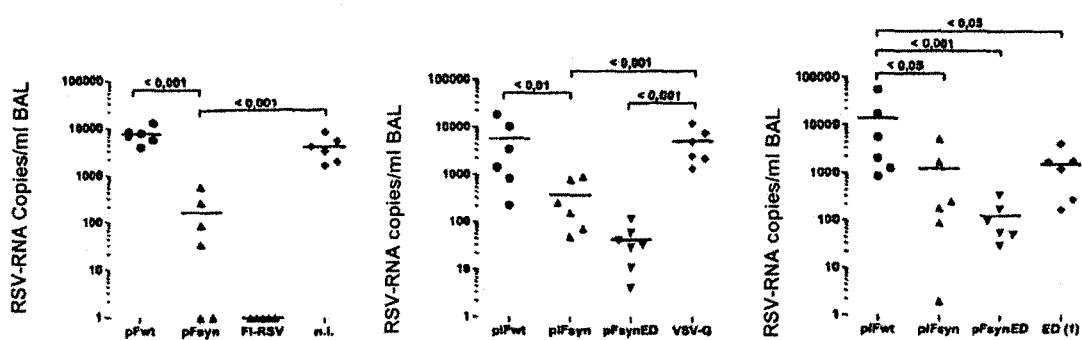
FIG. 1 shows the results of an RSV-qRT-PCR of RNA isolates from a bronchoalveolar lavage (BAL) of mice which were immunized with different plasmid DNA constructs. The numbers above the brackets indicate the statistical significance of the difference between the single results of the groups compared (Tukey test).

In a first aspect the subject matter of the present invention is a nucleic acid molecule which comprises a nucleic acid sequence coding for the F protein of the respiratory syncytial virus (RSV) or a fragment thereof, wherein this nucleotide sequence comprises SEQ ID NO: 1 or a fragment thereof. This sequence differs from the known sequences coding the F protein of RSV by a substitution of a nucleotide in the coding sequence. This substitution leads to a changed amino acid sequence of the F protein of RSV, in which a valine is present at position 241 instead of an alanine. This nucleic acid molecule can be used as a vaccine or as part of a vaccine composition.

"Fragment" in the context of a nucleic acid refers to parts of a nucleic acid sequence which, relative to this nucleic acid sequence, are shortened 3' and/or 5'. In particular, such fragments are at least 30, preferably at least 60, even more preferably at least 100 nucleotides long and code a part of an RSV F protein having a sufficient immunogenicity to elicit an immune response in an organism.

"Immunogen" or "immunogenicity" refers to the ability of a substance, for example of a peptide or of a protein, to elicit an immune response in an organism. The immunogenicity of a substance can for example be determined by the detection of antibodies.

In a further aspect the invention is directed to synthetic nucleic acid molecules derived from this nucleic acid molecule, said synthetic nucleic acid molecules having been codon-optimized for expression in a host organism, a host tissue or a host cell.

"Synthetic" in the context of a nucleic acid means, in the context of the present invention, that it is a nucleic acid molecule that does not naturally exist. One such synthetic nucleic acid molecule can for example be a codon-optimized nucleic acid molecule.

"Codon-optimized" in the context of a nucleic acid molecule refers to a nucleic acid molecule, the nucleotide sequence of which has been changed in such a way that the expression in a host organism is improved, i.e. a larger amount of the protein coded by the nucleic acid molecule is produced.

In the past, attempts to express the F protein of the respiratory syncytial virus (RSV) by transfection with polymerase II dependent DNA expression plasmids were not successful.

Eukaryotic cells differ from prokaryotic cells by a more pronounced compartmentalization of the intracellular space, which serves to enable complex enzymatic reactions necessary for an efficient protein expression, cell metabolism and/or cell division. The key for the replication of every virus is the adaptation to the host cell and, in particular, to its expression machinery. RNA viruses which replicate in the cytoplasm of their host cells have developed under the environmental conditions of the cytoplasm. These viruses thus have their own transcription machinery comprising an RNA-dependent RNA polymerase, which leads to the synthesis of mRNA from the genomic RNA. For this reason, cytoplasmic RNA viruses are not adapted to the complex nuclear milieu of the eukaryotic host cell. The inefficient expression of viral genes under the control of a eukaryotic promoter can thus be explained by the lack of elements required for the stabilization of the pre-mRNA, the mRNA-processing and/or the export out of the nucleus. The changing of the codon of viral genes to the codons which are most often used by the host cell allows the efficient expression of viral genes.

For this reason, the nucleic acid sequence with SEQ ID NO: 1 was transformed, consistent with this invention, into a synthetic, codon-optimized sequence, which leads to an identical translated sequence, but which uses alternative codons. Here, the method of the codon optimization comprises the following steps: identification of the placing of the codons for an exact open reading frame, comparison of the codon with the frequency of use in the desired host organism, in the event that the codon is not that most frequently used, replacement by the optimal codon for the expression, repeating this process for the entire gene segment, checking the new gene sequence for undesired sequences which were generated by the codon exchange, such as for example polyadenylation sites, undesired restriction sites, intron splice recognition sites, etc., assembly of the synthetic gene segments and testing of the expression in a host organism or a host cell.

One example for a synthetic nucleic acid sequence which was obtained by this method, and which has been codon-optimized for the expression in human cells is a nucleic acid molecule which comprises the nucleotide sequence of SEQ ID NO: 2 or consists of this. Another component of this invention are fragments of this nucleotide sequence which code for a part of the RSV F protein.

In comparison to the wild-type sequence with SEQ ID NO: 1, the inventors could observe, using the nucleotide sequence of SEQ ID NO: 2 in human cells, an improved expression of the F of RSV improved by a factor of 1000.

The codon-optimized sequences are then inserted into an expression cassette which additionally comprises sequences enabling the efficient expression of the coded protein in a host cell, preferably in a human cell. One such expression cassette then contains the codon-optimized nucleotide sequence with, functionally linked to thereto, associated transcription and translationcontrol sequences, such as for example a promoter and/or termination sequences.

The term "cassette" or "expression cassette" refers to the nucleotide sequences according to the invention, said nucleotide sequences containing nucleotide sequences which are to be expressed. Due to corresponding restriction sites at the 5'- and 3'-ends of the sequences, this cassette/expression cassette can simply be inserted into, removed from, or replaced in a vector or a plasmid. In addition to the coding nucleotide sequence, the expression cassette normally contains transcription and translationcontrol sequences, such as for example a promoter and/or termination sequences which are functionally connected with the nucleotide sequence and which allow expression in a host cell.

The term "promoter" in the sense of the present invention, refers to a region on a DNA strand, which allows recognition by the RNA polymerase. Following the recognition of the promoter region by an RNA polymerase, an initiation complex by the binding of the RNA polymerase in order to initiate transcription. This complex can be additionally modulated and regulated by additional activating sequences (enhancers) or inhibiting sequences (silencers).

A suitable promoter for the expression of the nucleotide sequences according to the invention is for example the CMV (cytomegalovirus) promoter. This can be functionally linked with the nucleotide sequence according to the invention in an expression cassette for the expression in human cells.

One such expression cassette which contains the nucleotide sequence according to the invention in connection with additional sequences required for the expression in a host cell, can be inserted into a vector.

The term "vector" refers to means with which DNA molecules can be introduced into a host organism or a host tissue or a host cell. There are different types of vectors including for example include plasmids, cosmids, viruses, e.g. adenoviruses, and bacteriophages.

A vector obtained in this way is also a component of the present invention. The vector is preferably a plasmid or a viral vector, in particular an adenoviral vector.

Such an adenoviral vector which contains the nucleotide sequence according to the invention can have a non-functional E1 gene region in order to prevent the replication of the virus and the generation of infectious virus particles in a host cell. Preferably, the E1 gene region is deleted and/or replaced by the inserted expression cassette. In addition, such a vector can also a deletion of the E3 gene region, which is normally responsible for dealing with host immunity. Such recombinant adenoviruses are, for example, known from U.S. Pat. No. 5,922,576 and can be reproduced in known cell lines ("packaging line") such as e.g. 293-, 911- or PerC.6 cells which express the viral E1 gene.

In order to produce such an adenoviral vector, the expression cassette which comprises the nucleotide sequence according to the invention can be inserted into a plasmid vector, e.g. via suitable restriction cleavage sites. Such a plasmid vector can comprise adenoviral nucleic acid sequences which allow homologous recombination with a suitable backbone plasmid containing a majority of the adenoviral genome. By recombination, one then obtains an adenoviral transfer (shuttle) plasmid which contains the nucleotide sequence according to the invention in the form of an expression cassette. Such an adenoviral transfer (shuttle) plasmid can for example also mediate a regulated expression of the inserted nucleotide sequence according to the invention. In this way, a large amount of adenoviral vectors can be produced. The adenoviral vectors can then subsequently be used as vaccine vectors.

For the preparation of adenoviral vectors expressing the F-protein, the CMV promoter can be replaced by a regulable promoter. With this, the vector can be expanded in cells which contain a regulation system for the expression of the RSV F-protein, for example the tetracycline regulated expression system (293TRex cells). For example, 293TRex cells are used for the production and the expansion of the adenoviral vector.

Regulable promoters are promoters which mediate a changed expression of the downstream transgene by means of substances, e.g. by means of antibiotics or of a protein that binds to a specific DNA sequence. Such regulable promoters are for example a CMV promoter with binding sites for the tetracycline repressor (tetracycline regulable promoter) or regulable expression mediated via the steroid ecdyson, but also other regulable expression systems.

The present invention thus also comprises in one aspect plasmids, for example the above described shuttle plasmid and adenoviral vectors which contain the nucleotide sequences according to the invention. The adenoviral vector preferably contains the nucleotide sequence with SEQ ID NO: 2 or a fragment thereof in form of an expression cassette with a promoter, for example the CMV promoter. Especially preferred is such a vector according to the invention of the adenoviral vector AdV-$F_{syn}$.

The molecular biological standard techniques for the preparation and the purification of DNA constructs of the invention, for the preparation of adenoviruses and adenoviral vectors and of the (shuttle) plasmids are known to one of ordinary skill in the art.

The adenoviral vectors or plasmids which contain the nucleotide sequence according to the invention can be administered to a subject, for example to a human, in order to induce an immune response against RSV.

For this reason the present invention relates in a further aspect to immunogenic compositions which comprise the nucleotide sequences with SEQ ID NO: 1 or 2 according to the invention or fragments thereof. In one such composition the nucleotide sequence according to the invention can be present in the form of the above-mentioned plasmids or vectors, preferably in the form of an adenoviral vector. One such vector allows the transport of the nucleic acid molecules according to the invention into a human host and the expression of the coded protein. Here, the protein is expressed in an amount which is sufficient to elicit the intended immune response.

Alternatively, the immunogenic compositions can also contain the protein coded by these nucleotide sequences.

Depending on the desired type of use, the immunogenic compositions can also contain a pharmaceutically acceptable carrier and/or excipient. Among other things, excipients also comprise known adjuvants.

The administration of the immunogenic compositions can take place in a manner known to one of ordinary skill in the art and includes oral dosing forms such as e.g. tablets, capsules, powder, granulates, solutions, suspensions, syrups and emulsions or alternatively injections, for example intravenous, intraperitoneal, subcutaneous or intramuscular. Intranasal or inhalative administration are also possible. All of these administration paths are known to one of ordinary skill in the art in the field. Preferred administration paths are oral, intranasal, inhalative, subcutaneous or intramuscular injection.

The formulation of the immunogenic compositions in a form which is suitable for the desired type of administration is known to the skilled person and can for example be taken from *Remington: the Science and Practice of Pharmacy* ("Remington's Pharmaceutical Sciences") of Gennaro A. R., 20$^{th}$ Edition 2000: Williams & Wilkins PA, USA. For example, the nucleic acid molecules according to the invention can be present in a physiologically acceptable solution, such as e.g. sterile saline or sterile buffered salt solution.

Also included is thus the use of the nucleic acid molecules, plasmids, vectors or proteins according to the invention for the preparation of a vaccine composition for the vaccination of a subject against diseases caused by infection with RSV. This subject is preferably a human. The vaccination can for example take place in a "prime and boost" method.

The amount of expressible DNA to be introduced into the recipient in a vaccination depends partially on the strength of the promoter used and the immunogenicity of the expressed gene product. In general, a dose of 1 ng to 100 mg preferably from about 10 µg to 300 µg is generally administered directly into the muscle tissue for an immunologically or prophylactically effective dose of a plasmid vaccine vector. An effective dose for recombinant adenoviruses are approximately $10^6$-$10^{12}$ particles, preferably $10^7$-$10^{11}$ particles.

A method for the preparation of the RSV F-protein, wherein the method comprises the expression of a nucleic acid molecule according to an invention in a suitable host cell, is also a component of the present invention. In a preferred embodiment of this method, the nucleic acid molecule according to the invention is codon-optimized for the expression in the host cell. This method comprises the transfection of a nucleic acid sequence according to the invention, for example in the form of a plasmid, into a suitable host cell, expression of the RSV-F protein in the host cell and, as the case may be, the isolation and purification of the RSV-F protein from the cells. The method is preferably an in vitro method.

A further aspect are polypeptide molecules obtained by the expression of the nucleic acid molecules with SEQ ID NO: 1 or 2 according to the invention or fragments thereof. In one embodiment these polypeptides comprise or consist of the amino acid sequence of SEQ ID NO: 3 or fragments thereof. As already mentioned above, these polypeptide molecules can also be contained in immunogenic compositions of the invention and can be used for vaccination.

"Fragment" in the context of a polypeptide refers to C- and/or N-terminally shortened proteins. The resulting peptides are preferably immunogenic and are at least 10 or more, preferably 20 or more, even more preferably 30 or more amino acids long.

The following examples serve to illustrate the invention in more detail and are not intended to restrict the invention in any way.

EXAMPLES

Example 1

Cultivation of RSV

The passage of RSV was performed with Hep2 cells and was stored at ±80° C. Hep2 or 293T cells were infected by addition of cell supernatant containing RSV. Two hours after the addition of the virus, the supernatants were removed and the cells were supplied with DMEM medium containing 0.5% fetal calf serum (FCS) and 100 µg/ml penicillin G and streptomycin sulfate.

Example 2

Preparation of the RSV-F Expression Plasmid

For the preparation of the RSV-F expression plasmid, cytoplasmic RNA was isolated from RSV infected Hep2 cells using the Qiagen Rneasy® Minikit. Following reverse transcription (ThermoScript™ RT-PCR system, Invitrogen) the RSV cDNA was amplified by PCR (primers: sense: 5'-[G A T C C A A G C T T C C A C C] A T G G A G T T G C C A A T C C T C A A A; antisense: 5'-[T C G A C C T C G A G] T T A G T T A C T A A A T G C A A T A T T A T T T A T A C C) using the Platinum® Taq DNA Polymerase (Invitrogen). The 1.7 kb fragment was subcloned into the pcDNA3.1(+) vector (Invitrogen).

The codon-optimization of the open reading frame (ORF) of the wild-type was performed by the firm Geneart (Regensburg, Germany). Here, synthetically prepared oligonucleotides were ligated and the resulting fragment was cloned into the pUC57 plasmid and sequenced.

The codon-optimized ORF was subcloned into the pcDNA3.1(+) vector (Invitrogen) and the pI vector via HindIII/XhoI restriction. The deletion of the stop codon of the RSV-F ORF was performed with PCR mutagenesis. The sequence of all plasmids was confirmed by sequence analysis (Genterprise, Mainz, Germany).

Example 3

Cell Transfection 293T and Hep2 cells were cultivated in Dulbecco's modified Eagle's medium (Invitrogen) supplemented with 10% fetal calf serum (Invitrogen), penicillin G and streptomycin sulfate in a respective end concentration of 100 μg/ml. The cells were transfected in 25 cm$^2$ flasks with 5 μg of the plasmid DNA prepared in example 2 by means of the calcium phosphate co-precipitation method as described by DuBridge et al. (DuBridge et al. (1987) Analysis of mutation in human cells by using an Epstein-Barr virus shuttle system. *Mol. Cell Biol.*, 7, 379-387).

Example 4

Figure 13:
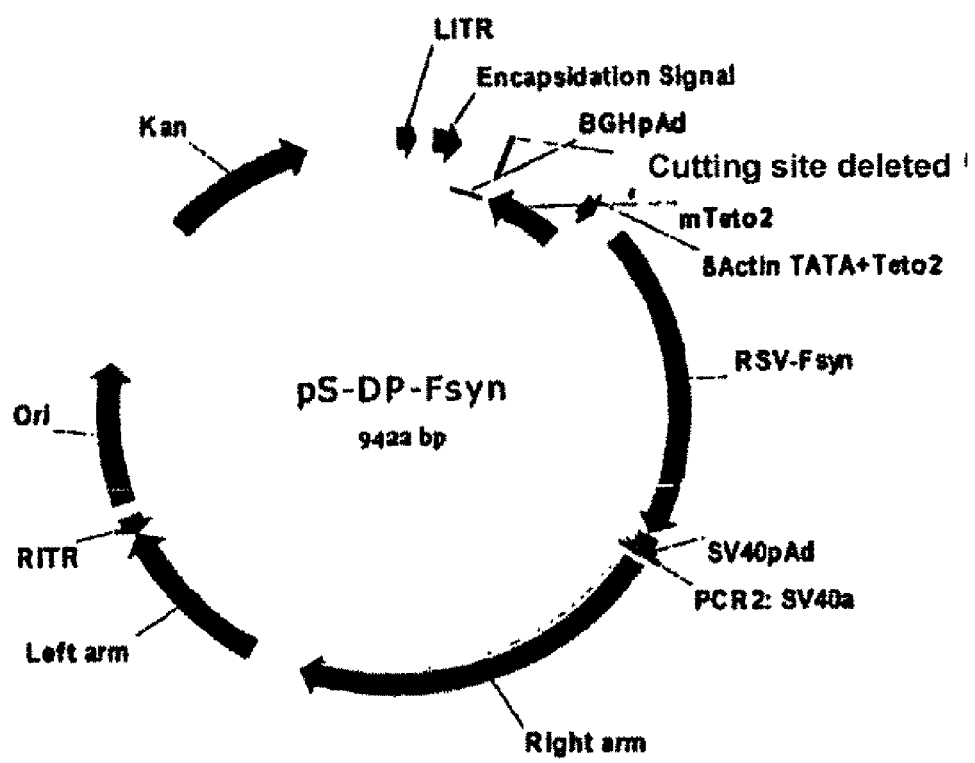
FIG. 13 shows the vector map of a shuttle plasmid into which the codon-optimized RSV-F was cloned via the restriction sites HindIII and XhoI or of a shuttle plasmid which was used for incorporation of codon-optimized RSV-F, and which contains a tetracycline-dependent promoter (pS-DP-delta). This promoter is shut off via a genetic switching element in 293TRex-cells (Invitrogen).
Figure 13:
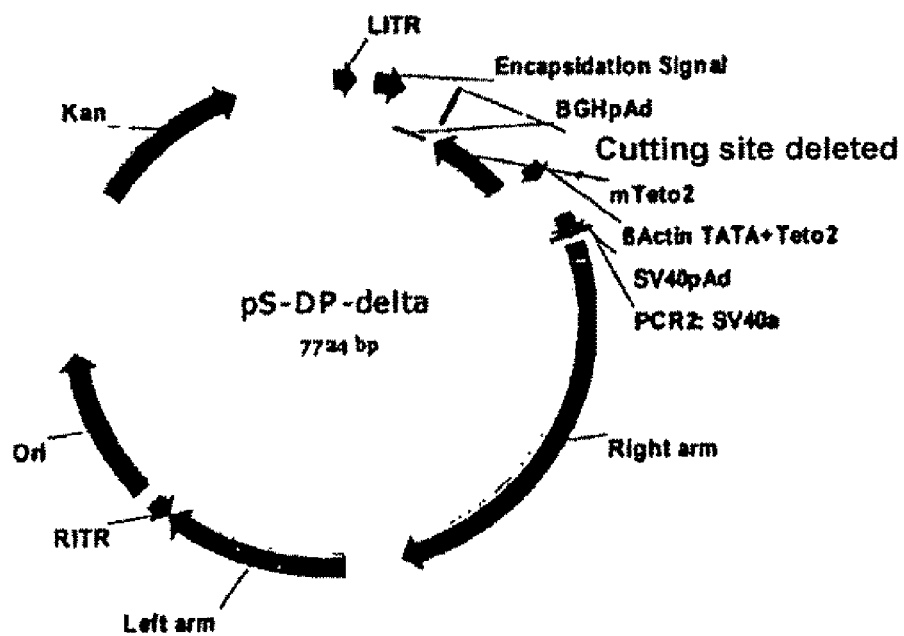

Homologous Recombination by Means of Electroporation and Preparation of Electrocompetent BJ5183 Bacteria The method of homologous recombination was used for the preparation of recombinant adenoviral vectors. A linearized shuttle vector (FIG. 13) and an adenoviral vector (pAdEasy-1; Q BIOgene, Carlsbad, Calif. USA) were co-transformed by means of electroporation. Due to homologous arms in the plasmid, a recombination took place in BJ5183 bacteria; the resulting plasmid carried a kanamycin resistance, whereby positive clones could be selected on an LB$_{Kan}$ agar plate. One such vector system is for example also available under the name AdEasy™ from Q BIOgene (Carlsbad, Calif., USA).

For the preparation of electrocompetent BJ5183 bacteria a fresh colony or a frozen stock of the bacteria were cultured overnight in 10 ml LB-medium with streptomycin; this pre-culture was used to inoculate a 1 l culture. The bacteria were shaken at 37° C. in a horizontal shaker at 200-220 rpm to an OD$_{600}$ of 0.6-0.8 (approximately 3 hours). After that the cells were collected in a centrifuge cup and were incubated for 60 minutes on ice. After the incubation, the cells were pelleted at 2,600 g and 4° C. for 10 minutes and were then washed with 1 l of ice cold water with 10% glycerol and were pelleted for 30 minutes. After repeating the washing step, the cells were resuspended in 20 ml residual volume and were transferred into a 50 ml container and were once again pelleted for 10 minutes. Now the cells were resuspended in 3-5 ml residual volume, aliquoted, frozen in liquid nitrogen and stored at −80° C.

For the homologous recombination 40 μl BJ5183 bacteria were furnished on ice in a cooled electroporation cuvette and approximately 100 ng plasmid DNA of the adenoviral vector and approximately 1 μg plasmid DNA of the shuttle vector were pipetted thereto. The electroporation proceeded at a voltage of 2500 V. Following addition of 300 μl SOC medium, the bacteria were incubated at 37° C. for 1 h in a shaking apparatus and were subsequently plated out onto LB$_{Kan}$ plates overnight.

The DNA was isolated in analytical scale from the grown clones and checked. Upon positive recombination it was re-transformed in DH5α bacteria to prevent further recombination events. To this end, 1 μl DNA was added to 50 μl DH5α bacteria and electroporated.

Example 5

Preparative Recovery of the Plasmid DNA Cloned In Vitro or Recombined in BJ5183 Bacteria The *Escherichia coli* strains XL2-Blue (Stratagene) and DH5α (Invitrogen) served for the preparative recovery of the plasmid DNA cloned in vitro or recombined in BJ5183 bacteria. By means of a resistance gene the plasmids which were used allowed selection by corresponding antibiotics (ampicillin or kanamycin). The transformed bacteria were selected on LB agar plates and in LB liquid medium with an addition of the respective antibiotic. 3 ml of overnight cultures which were incubated at 37° C. in a horizontal shaker served as a pre-culture for the preparative plasmid isolations. For the extraction of larger quantities of DNA, 100 ml or 250 ml of LB medium were incubated with 1 ml of a pre-culture in sterile Erlenmeyer flasks and were incubated at 37° C. overnight in the horizontal shaker at 200-220 rpm.

Example 6

Calcium Phosphate Transfection of Cells

For growing adenoviral vectors, the prepared adenoviral plasmids (following linearization by PacI digestion and subsequent purification by phenol/chloroform extraction) had to be transfected in T-REx™-293 cells (Invitrogen). To this end, the method of the calcium phosphate co-precipitation was used, wherein the DNA binds to the cell membrane via salt complexes and is taken up.

1 day before the transfection, 800,000 T-REx cells were taken out of a logarithmically growing culture, were seeded with 5 ml medium into a fresh 25 cm$^2$ cell culture flask and were incubated overnight at 37° C. in the incubator.

At the time of transfection, the cells were approximately 50% confluent. 1-4 hours before the transfection, the cell culture medium was replaced with fresh medium. 15-20 μg DNA with 169 μl sterile H$_2$O were furnished on ice for the transfection. To this were pipetted 31 μl of 2 mM CaCl$_2$ and were carefully mixed. 250 μl 2×HBS buffer solution were added drop-wise to the H$_2$O-DNA-CaCl$_2$ mixture at room temperature. The subsequent ten-minute incubation at room temperature enabled the formation of a milky precipitate. Following this, the transfection mixture was mixed once again and dripped into the cell culture medium.

After a maximum of 18 hours incubation in the incubator, the medium was changed, since the CaCl$_2$ can be toxic to the cells.

The plasmid for AdV-eGFP (adenoviral vector which expresses the eGFP protein) was in each case transformed in parallel into a second cell culture bottle, so that the success of the transfection and the progress of the production of adenoviruses could be monitored in the fluorescence microscope by the developing fluorescence of infected cells. Generally all cells were completely lysed one week later, and the supernatant with the produced adenoviruses was taken off and could be used for the next infection for further growing the adenoviral vectors.

Example 7

Growing of Adenoviruses

The adenoviral vectors were grown in T-REx™ 293 cells (Invitrogen). This cell line was chosen since its tetracycline-regulated expression system rendered it suitable for the cultivation of adenoviruses expressing a cell-toxic gene such as the fusion protein of RSV. For instance, when propagating adenovirus in other cell lines, the expression of the RSV-F protein leads to the formation of syncytia in the cell culture, reducing the virus production. In contrast, in the T-REx cells the expression of the RSV-F protein in the virus reproduction is suppressed in the absence of tetracycline, and the viral yield is significantly higher.

The growth of adenoviruses in T-REx cells proceeded via multiple infection cycles. In each of the first passages, a 75 cm$^2$ cell culture bottle was infected, in each of the later a 175 cm$^2$ cell culture bottle. For infection, 3-8 ml of the cell culture supernatant harvested in the prior passage was in each case used in a suitable amount of fresh medium. At the time point of infection the cell cultures were about 75% confluent. In the first four hours after addition of virus, the cells were regularly rotated in order to increase the rate of infection. This was followed by a change of medium (10-15 ml medium in a 75 cm$^2$ bottle, 20 ml in a 175 cm$^2$ bottle).

The progress of the infection was checked daily and was visible by the CPE (cytopathic effect), which can be seen as a separation of the cells. Harvest of the virus took place after 3-6 days, as soon as all cells were completely infected and washed away. Here, the cell culture supernatant was removed and was subsequently alternately frozen at −80° C. and thawed in a 25° C. water bath three times so that the cells which had not yet burst would also release the adenoviruses produced. After the three freeze/thaw cycles the cell debris was centrifuged off at 1000 g and 4° C. for 10 minutes. The supernatant with the adenoviruses was stored at −80° C. and was used for the next infection.

The adenoviral vectors were passaged in T-REx cells until as high as titer as possible (determined according to the GTU method) of ideally at least 10$^{10}$ GTU/ml was reached. Only then were 2-3 175 cm$^2$ cell culture bottles infected and, with the supernatant harvested therefrom, 5 or 10 175 cm$^2$ cell culture bottles, in order to obtain enough starting material for the subsequent virus purification.

Example 8

Purification and Concentration of Adenoviruses

The purification and concentration of the adenovirus vectors proceeded with the Vivapure® AdenoPACK™ 100 kit (Sartorius) according to the instructions of the manufacturer. Here, a concentration by a factor of 1000 was achieved. The buffer exchange step was performed in the context of the final concentration, wherein the recovered adenoviruses were taken up in storage buffer.

Example 9

Determination of Titer of Adenoviral Preparations

For the determination of titer of adenoviral vectors, two different methods were used.

In the determination of the OPU (optical particle units), the titer of the adenoviral preparations were calculated via a photometric DNA determination. For this, all DNA-containing viral particles is ascertained, meaning also defective particles which are not infectious or which do not carry the desired gene. Advantages of the OPU determination are that this method of determining the titer is the fastest and is the most reproducible.

For the determination of the OPU a dilution series with, for example, the dilutions 1:2, 1:5, 1:10, 1:20, 1:25 and 1:50 were prepared from the adenoviral preparation. Here, the purified adenoviruses were in each case diluted in virion lysis buffer (0.1% SDS 10 mM Tris-HCl pH 7.4, 1 mM EDTA in H$_2$O). For each dilution stage, a blank solution was prepared in which storage buffer (10% glycerin in Dubecco's modified PBS) (instead of the adenoviral preparation) was analogously diluted in virion lysis buffer. Following an inactivation of the virus-containing samples at 56° C. for ten minutes, the absorption of the dilutions at the wavelength $\lambda$=260 nm (OD$_{260}$) was measured, wherein the photometer in each case was previously set with the corresponding blank solution. The OPU was subsequently determined from the OD$_{260}$ values according to the following formula in which the value of 1.1×10$^{12}$ [74] was chosen as the extinction coefficient:

OPU/ml=OD$_{260}$×dilution of the preparation×1.1×10$^{12}$

Here, the OPU was determined as the average of the values measured for the individual dilutions.

Since the OPU (as described above) also includes defective particles, the GTU (gene transducting units) was additionally determined, in other words the fraction of the infectious and gene transducing, and thus of the desired, adenoviral vectors by the OPU, by means of a serial dilution series on 293A cells with subsequent specific immune cytochemical staining of the RSV-F protein expressed on infected cells.

The titration was performed on 293A-cells. To this end, a 96-well plate of type F with approximately 10,000 293A-cells (in 100 µl medium) per well was loaded and cultivated in the incubator. The titer plate was infected one day later. Here, the adenoviral preparation was added into the first well of the titer plate in the ratio 1:1000 (10 µl of a 1:100 pre-dilution were added to the 100 µl medium in the first well) and further serially diluted from well to well 1:10 in a horizontally successive fashion (in each case 10 µl were transferred from well to well). This dilution series was performed repeatedly in 3-5 series. 2-3 series remained virus-free as a negative control and were analogously diluted.

A specific immune cytochemical staining of the F-protein of RSV was performed 2-3 days after the infection of the titer plate. This was directly possible in testing the adenoviral vector Adv-F$_{syn}$ (adenoviral vector containing the nucleotide sequence of SEQ ID NO: 2), since the infected cells express the RSV-F protein on their surface.

In the first step of the staining of the titer plate the medium was removed and the cells were fixed for ten minutes with 100 µl 80% ethanol per well. After removal of the ethanol the plate was air dried. Then 200 µl PBS-T$_{0.05\%}$ (0.05% (v/v) Tween 20 in PBS) were placed into every well for rehydration and were left on the plate for 5 minutes. The plate was knocked empty and then 100 µl of a 1:250 dilution of the 18F12 primary antibody in PBS-T$_{0.05\%}$ were placed into every well. The plate was subsequently incubated for 1 hour at 37° C. Here, the 18F12 antibody, which is directed against the F-protein of RSV, binds to the F-protein expressed on the infected cells. Non-bound antibody was removed in a 3× washing step performed three times with PBS-$T_{0.05\%}$. Rabbit anti-mouse immunoglobulin $PO_{260}$ (Dako), which binds to the monoclonal 18F12 antibody, was used for the detection of the primary antibody as an enzyme-coupled secondary antibody, and was diluted 1:400 in PBS-$T_{0.05}\%$. 100 µl of this solution were placed into every well, the plate was once again incubated for 1 hour at 37° C. After a washing step performed three times with PBS-$T_{0.05\%}$, the staining reaction mediated by the enzyme bound to the secondary antibody was initiated by addition of 100 µl of the staining solution (200 µl AEC (3-amino-9-ethylcarbazol 10 mg/ml dissolved in 96% ethanol) and 10 µl $H_2O_2$ in 10 µl phosphate-citrate) into every well. The staining reaction took place in an incubation at 37° C. for 30 minutes and was stopped by addition of 100 µl $H_2O$ per well after knocking empty the plate.

The interpretation was performed under the microscope, in that for every series the number of the stained cells in the last well in which an infection could still be demonstrated by staining, was determined and was multiplied by the dilution stage applicable for this well. The GTU is calculated based on the average of all rows.

The staining method described above refers to the determination of titer of preparations of adenoviral vectors expressing RSV-F protein. In contrast, in the determination of the titer of a preparation of AdV-eGFP, no staining was performed, the titer plate was evaluated by counting the green luminescent cells as observed by fluorescence microscopy.

Example 10

Immunization Study in BALB/c Mouse Model

In the context of a first immunization study, a group of 6 BALB/c mice were subcutaneously immunized with $1\times10^8$ GTU ($5\times10^9$ OPU) AdV-$F_{syn}$. A boost followed after four weeks. As a comparison, one group of, also, six mice were subcutaneously immunized with plasmid DNA. Here, the plasmid pcDF$_{syn\ ED}$ was used, which codes for the ectodomain of the synthetic F-protein RSV and in pre-studies with BALB/c mice had induced the best protection following DNA immunization against RSV (FIG. 1) as compared to the plasmids pcIF$_{syn}$ and pcIF$_{wt}$, which code for the synthetic F-protein (full length) and the wild-type F-protein of RSV, respectively. Here, FI-RSV served as a control of the induction of the immune response against RSV and denotes the RS-viruses which were used for the immunization and inactivated with formalin. As control groups, 6 mice were immunized subcutaneously with AdV-OVA (adenoviral vector which expresses ovalumin), and 3 mice were not immunized at all. The mice were infected three weeks after the second immunization with about $1\times10^7$ i.E. (infectious units) of plaque-purified RSV.

Figure 2:
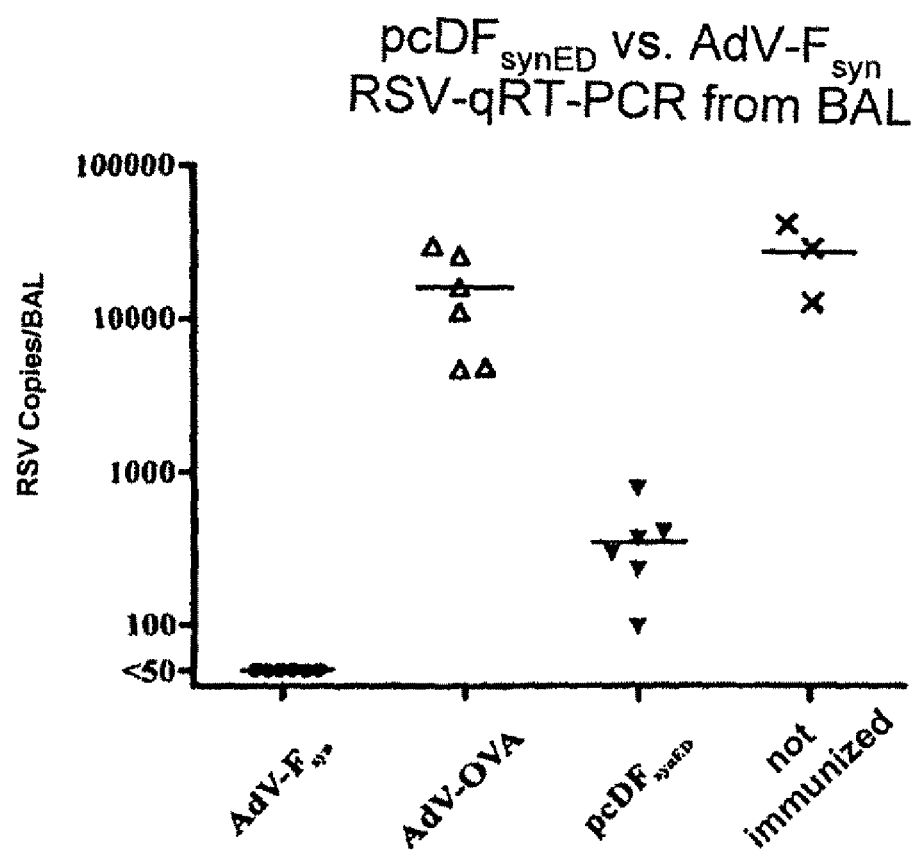
FIG. 2 shows the results of an RSV-qRT-PCR of RNA isolates from a bronchoalveolar lavage (BAL) of mice which were immunized with different constructs after infection with RSV. The copy number of RSV following qRT-PCR was standardized by RNA quantification and is shown here for the RNA recovered of the BALs obtained. The individual values from 6 mice (black symbols) as well as the average value (bars) are shown for each of these.

Following anesthetization the mice were killed on day 5 after infection and a BAL (bronchoalveolar lavage) was obtained. The viral RNA was extracted from the BAL and the content of RSV RNA was determined by means of quantitative RT-PCR as a measure of the protection of the animals. A high RSV load was determined in the control groups, with on average approximately 20,000 copies of RSV. While the RSV copy number was already significantly reduced by a factor of about 55 (on average 360 copies per BAL) following immunization with pcDF$_{syn\ ED}$, following immunization with AdV-$F_{syn}$ no more RSV could be detected at all in any mice of the group, meaning that the RSV load was reduced here by a factor of at least about 400, since the limit of detection of qRT-PCR is 50 copies. Following vaccination with pcDF$_{syn\ ED}$, the animals are thus only somewhat protected from RSV, since RSV replication in the lungs of the mice is only inhibited but not completely prevented. In contrast, following vaccination with AdV-$F_{syn}$, the animals appear to be completely protected since RSV can no longer be detected (FIG. 2).

In the course of the experiment, blood was taken from the mice in week 0 (before the first immunization) and 7 (after the second immunization) as well as on the day of killing, and serum was obtained from this. In this first immunization study, an additional removal of blood was not yet performed following the first and before the second immunization.

The titer of RSV-specific IgG1 and IgG2a antibodies in the blood of the mice was determined by means of the serum samples in antibody ELISA. Since a standardization of this ELISA was hitherto impossible, the results here can only be compared within the groups of one immunization study. Here, all samples of an immunization study were investigated simultaneously on one ELISA plate.

Figure 3:
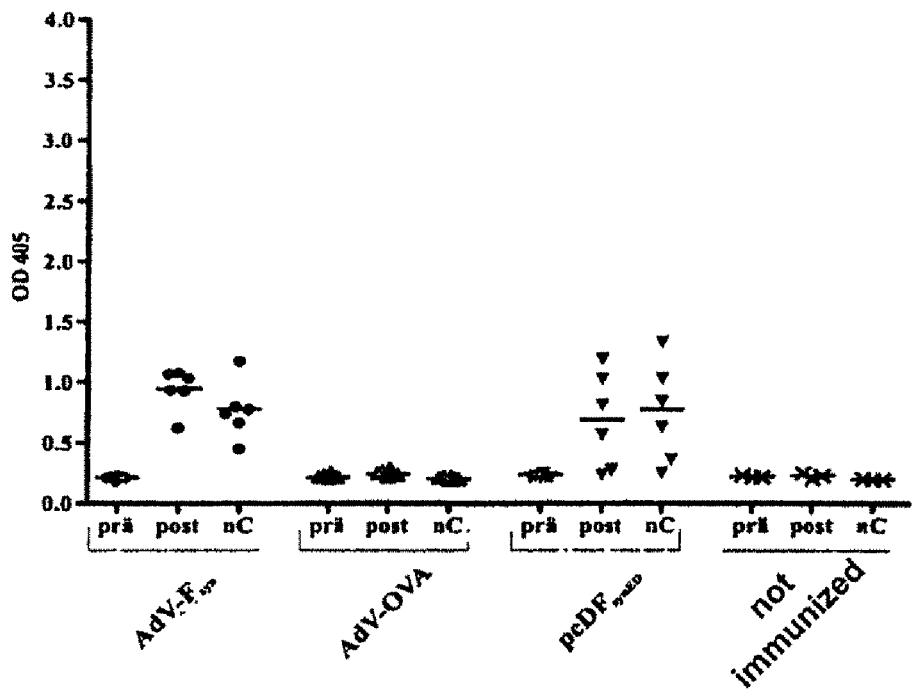
FIG. 3 shows the results of an IgG antibody ELISA. The serum samples obtained before the first immunization (prä), after the second immunization (post) and after the challenge (approximately $1 \times 10^7$ iE (infektiöse Einheiten; Engl.: infectious units) of RSV purified from plaque, intranasal) on the day of death (nC) of mice immunized with different compositions (AdV-$F_{syn}$: for the synthetic codon-optimized) F-protein of RSV-coding nucleic acid in adenoviral vector; AdV-Ova: adenoviral vector with nucleic acid which codes for ovalbumin; pcDF$_{syn\_ED}$: plasmid which codes for the ectodomain of the synthetic (codon-optimized) F-protein of RSV) or of non-immunized mice were tested in the IgG antibody ELISA for RSV-specific IgG1- and IgG2a-antibodies. The intensity of the absorption at the wavelength 405 corresponds to the antibody titer in the blood of the mice. Each of the individual values from 6 mice (black symbols) as well as the average value (bars) are shown.
Figure 3:
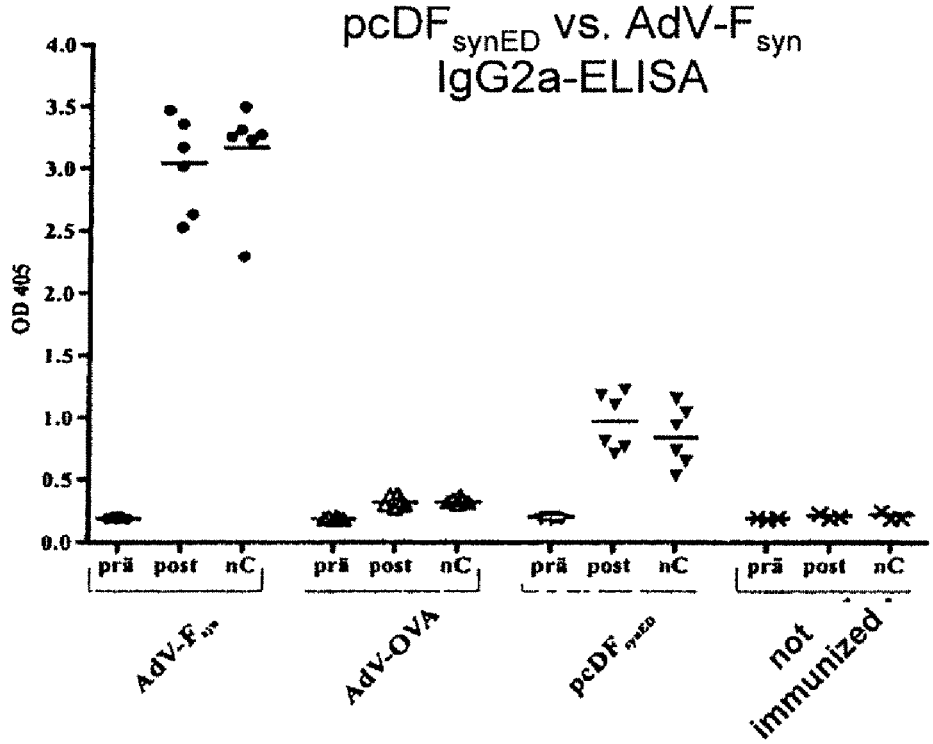

RSV-specific IgG1 or IgG2a antibodies could not be detected in any mice group prior to immunization. In the control groups the titer remained identically low over the course of the experiment. In contrast, a clear increase in the RSV-specific antibodies could be shown with the AdV-$F_{syn}$ or with pcDF$_{synED}$ vaccinated mice after the second immunization and on the day of death. While the IgG1 antibodies in both groups increased in similar manner, the increase in the IgG2a antibodies following vaccination with AdV-$F_{syn}$ was many times stronger than following vaccination with pcDF$_{synED}$. The two fold immunization with AdV-$F_{syn}$ thus effects a strong immune response with regard to the formation of systemic RSV-specific IgG antibodies and, in this context, induces the production of much more IgG2a than following twofold immunization with pcDF$_{synED}$ (FIG. 3). The fact that the IgG2a antibodies increased many times more strongly than the IgG1 antibodies in the AdV-$F_{syn}$ vaccinated mice indicates a $T_H1$-based immune response following immunization with AdV-$F_{syn}$, which can be judged as particularly positive, since the disease exacerbation observed in the 1960s following immunization experiments with formalin-inactivated RSV was primarily attributed to a shifting of the immune response in favor of a $T_H2$ response.

Figure 4:
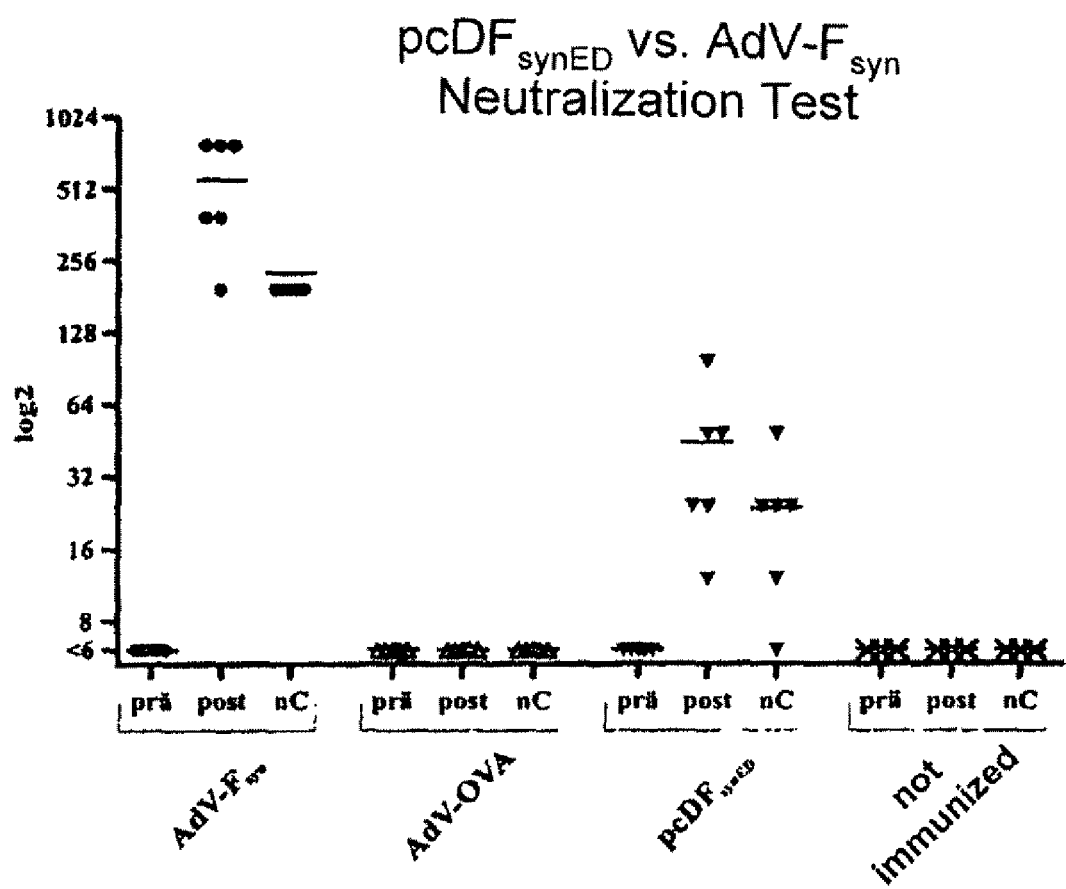
FIG. 4 shows the result of a neutralization test. The serum samples of the mice obtained before the first immunization (prä), after the second immunization (post) and after the challenge on the day of death (nC) were serially diluted and then the dilution series was tested in the neutralization test for neutralizing antibodies against RSV. In each case, the highest serum dilution at which the infection by RSV is inhibited by neutralizing antibodies to 50% (IC50) is shown. Each of the individual values from 6 mice (black symbols) as well as the average value (bars) are shown.

The sera of the mice were additionally tested in the neutralization test for neutralizing antibodies against RSV. No neutralizing antibodies were present in any mice group at the beginning of the experiment. While no neutralizing antibodies against RSV could be found in any of the serum samples of the control groups, the immunization with AdV-$F_{syn}$ or pcDF$_{synED}$ led to the formation of neutralizing antibodies. Here, these increased following AdV-$F_{syn}$ vaccination about 13 times more strongly than following vaccination with pcDF$_{synED}$, so that, here as well, the immunization with AdV$_{syn}$ can be viewed as superior to the vaccination with pcDF$_{synED}$. In comparison to the serum samples following the second immunization, a slight reduction in the titer of neutralizing antibodies could be observed in each of the serum samples from the day of killing, meaning following challenge, which can be explained by a consumption of these over the course of the infection (FIG. 4).

In the immunization studies performed, the superiority of AdV-$F_{syn}$ over pcDF$_{synED}$ could thus be clearly shown (induction of a higher titer of RSV-specific antibodies, lower RSV load in the lung and correspondingly better protection of the mice).

Example 11

Immunization with AdV-F$_{syn}$ Via Different Administration Routes

This experiment is intended to investigate the influence of administration route on the immunization with AdV-F$_{syn}$. To this end, three groups, each of 6 BALB/c mice, were immunized with 1×10$^8$ GTU (5×10$^9$ OPU) Adv-F$_{syn}$, wherein the vaccine was administered intranasally to the first group, intramuscularly to the second and subcutaneously to the third. A fourth group, also of 6 BALB/c mice, was not immunized and served as a negative control. The timeline for vaccinations, blood removal and challenge was adopted from the first immunization study (see example 10).

Figure 5:
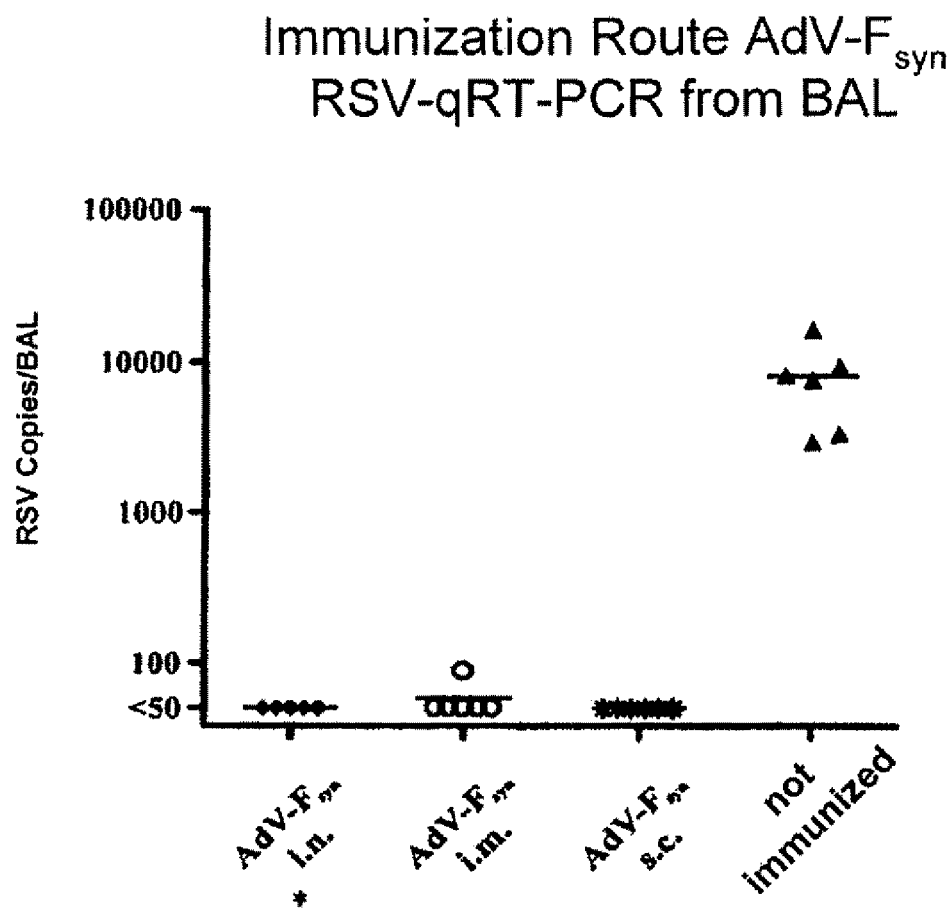
FIG. 5 shows an RSV-qRT-PCR of RNA isolates from a bronchoalveolar lavage (BAL) of mice which were immunized via different administration paths with an adenoviral vector according to the invention, said adenoviral vector comprising a nucleic acid molecule coding for a codon-optimized RSV-F protein. The copy number of RSV according to qRT-PCR was standardized by RNA-quantification and is shown here for the RNA isolates of the BALs obtained on the day of death. Also shown are each of the individual values from 6 mice (black symbols) as well as the average value (bars).

On the day of killing (5 days after infection) the BAL of the mice was obtained. Following isolation of viral RNA from the BAL, the content of RSV RNA was determined by means of quantitative RT-PCR in order to make a statement regarding the protection of the animals following vaccination. While the RSV load in the non-immunized control group was very high, all three of the mouse groups immunized with AdV-F$_{syn}$ showed a very good protection. With the exception of a single mouse from the intramuscularly vaccinated mouse group, in which the RSV load in the BAL was 88 copies, no RSV load was detectable in any BAL, meaning that all mice were very well protected following vaccination with AdV-F$_{syn}$ irrespective of the administration route (reduction by a factor of at least 160 in all three mice groups) (FIG. 5).

Figure 6:
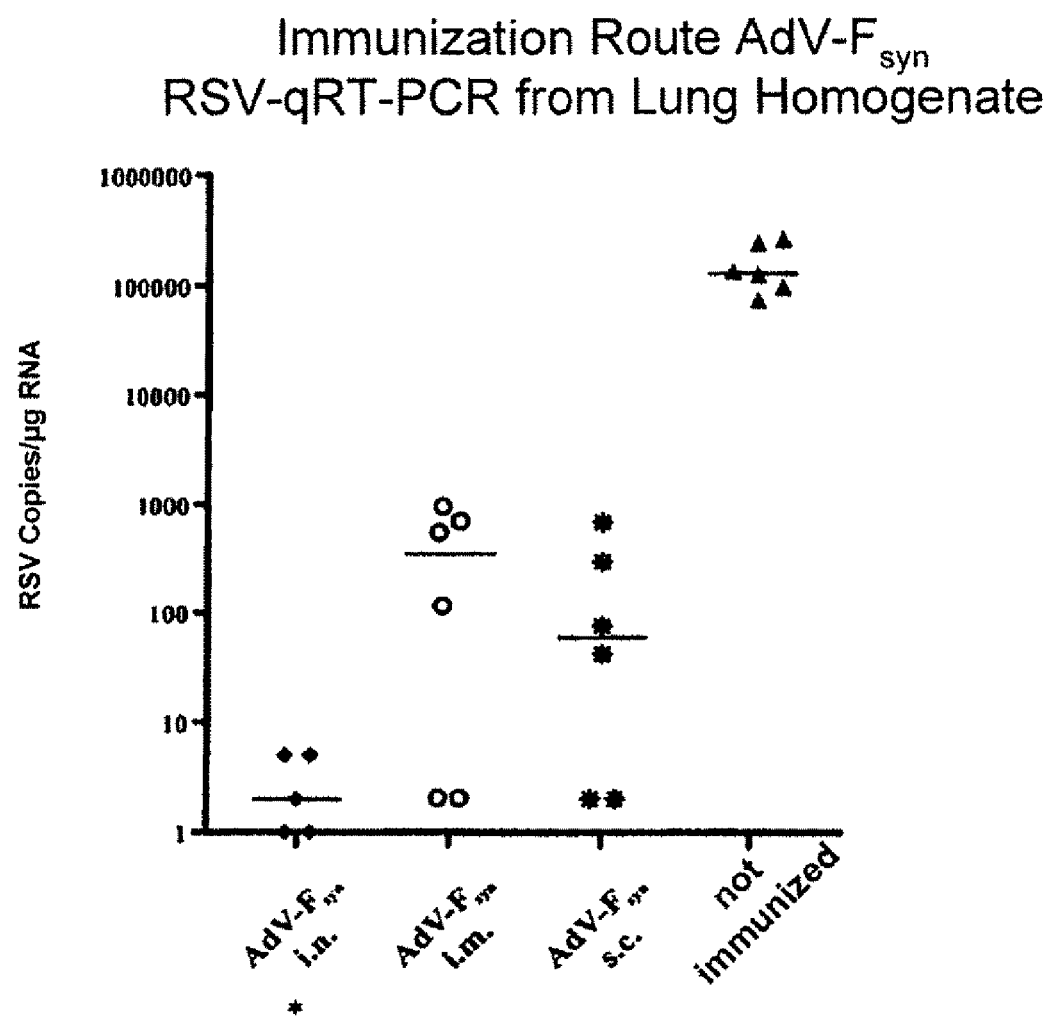
FIG. 6 shows an RSV-qRT-PCR from RNA isolates from the lung homogenate of mice which were immunized by different administration paths with an adenoviral vector according to the invention, said adenoviral vector comprising a nucleic acid molecule coding for a codon-optimized RSV-F protein. The results of the qRT-PCR from the RNA isolates of the lung homogenates obtained on the day of death are shown. The copy number of RSV according to qRT-PCR was standardized by RNA quantification and converted relative to the RNA content of the isolates. Each of the individual values of 5 (*) or 6 mice (black symbols) as well as the average value (bars) are shown.

Since no differences with regard to the RSV load in the lungs of the different mice groups could be determined by quantitative RT-PCR performed based on the RNA isolates from the BALs of the mice, the total RNA from the lung homogenate, which had also been obtained on the day of killing, was additionally isolated. These RNA isolates were also tested in the quantitative RT-PCR for their RSV content in order to obtain a second value for the RSV load in the mice lungs, and thus for the protection of the mice from RSV. Here, the results of the qRT-PCR were subsequently converted in relation to the RNA content of the RNA isolate, since in the RNA isolation not only viral RNA, but also total RNA was isolated. In this way, an RSV copy number of on average approximately 160,000 copies/μg RNA was determined by quantitative RT-PCR in the non-immunized control group. The determination of the RSV load based on RNA isolates from the lung homogenate is thus significantly more sensitive than that based on the RNA isolates from the BAL, where in the non-immunized control group an RSV load of on average approximately only 8,000 copies/BAL was found. Corresponding differences in the immunized mice groups were also observed. The best protection was achieved following intranasal immunization with AdV-F$_{syn}$. Here, the RSV load in all mice was below the level of detection of 50 copies by qRT-PCR. Converted in relation to RNA content of the samples, this means that the intranasally vaccinated animals showed only a very low RNA load. Even assuming 50 copies as the result of qRT-PCR, 1 animal was completely protected, while the other 5 animals had 1-5 copies/μg RNA. Thus, very good, nearly complete protection from RSV is induced by intranasal immunization, wherein the RSV load is reduced by a factor of approximately 70,000. In contrast, following intramuscular and subcutaneous vaccination with AdV-F$_{syn}$, an RSV load was detectable by qRT-PCR. From each group, only 2 animals with an RSV load of 2 copies/μg RNA were very well-protected; each of the other 4 animals showed an average RSV load of approximately 570 copies/μg RNA following intramuscular vaccination (approximately 280-fold reduction) or approximately 275 copies/μg RNA following subcutaneous vaccination (approximately 580-fold reduction), respectively (FIG. 6). In an immunization with AdV-F$_{syn}$, the intranasal route is thus clearly the best suited to induce very good protection from RSV.

The sera of the mice recovered over the course of the experiment were again tested in the IgG antibody ELISA and in the neutralization test for the induction of systemic RSV-specific antibodies.

Figure 7:
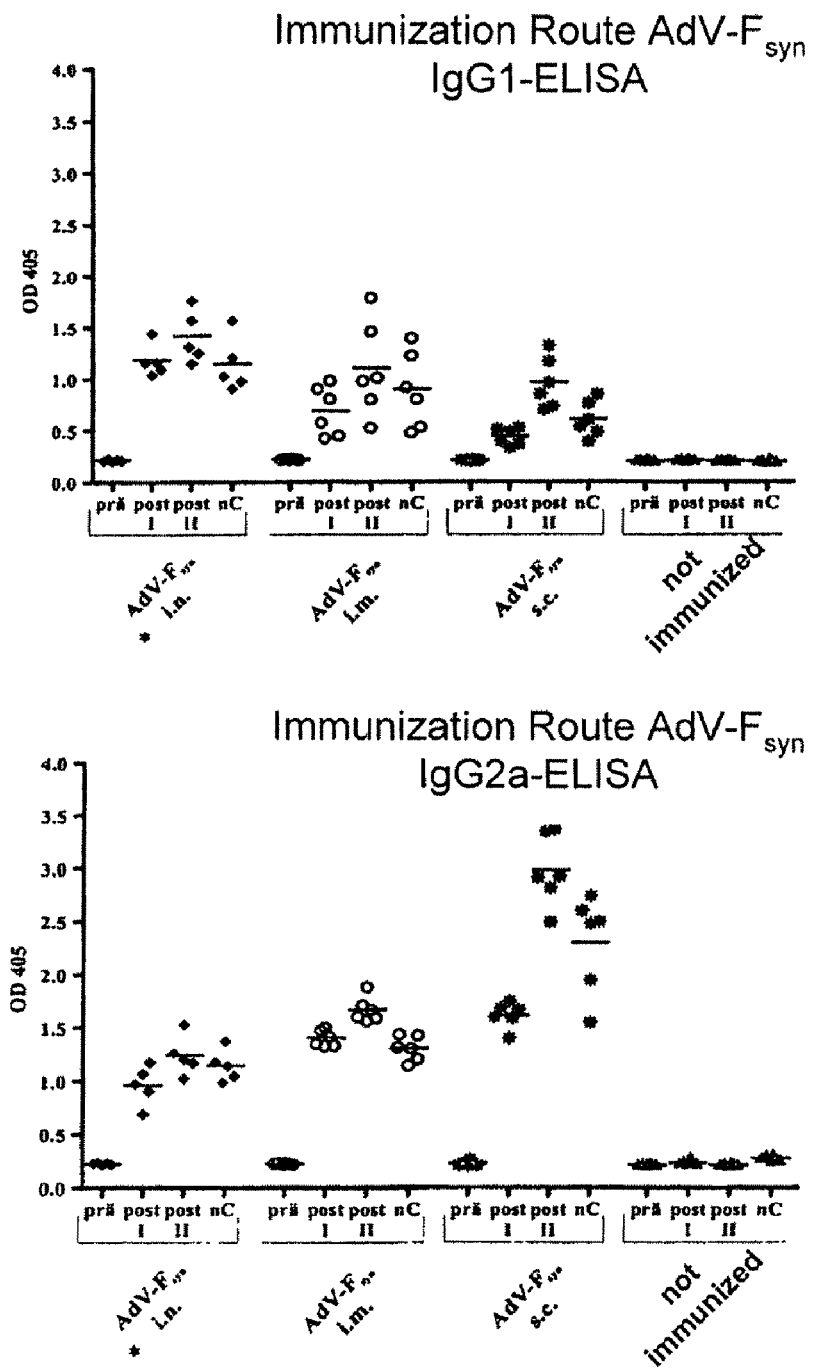
FIG. 7 shows an IgG antibody ELISA of mice which were immunized by different administration paths with an adenoviral vector according to the invention, said adenoviral vector comprising a nucleic acid molecule coding for a codon-optimized RSV-F protein. The serum samples of the mice obtained before the first immunization (prä), after the first immunization (post I), after the second immunization (post II) and after the challenge on the day of death (nC) were tested in IgG antibody ELISA for RSV-specific IgG1- and IgG2a-antibodies. The intensity of the absorption at the wavelength 405 corresponds to the antibody titer in the blood of the mice. Each of the individual values of 5 (*) or 6 mice (black symbols) as well as the average value (bars) are shown.

Prior to the immunization, RSV-specific IgG1 or IgG2a antibodies were not detectable in any mouse group. In the control group, the titer remained similarly low even in the further serum samples. In contrast, a clear increase in the RSV-specific titer was observed not only for IgG1 but also for IgG2a antibodies in the three mouse groups vaccinated with AdV-F$_{syn}$. Here, this increase was dependent on the route of administration of AdV-F$_{syn}$, since the antibody titer in the intranasal (i.n.), intramuscular (i.m.) and subcutaneous (s.c.) vaccinated mice each came out differently. Here, the titer of primarily the IgG2a antibodies varied quite strongly, the subcutaneous immunization led to an increase in IgG2a antibodies which was many times stronger than the intranasal or the intramuscular vaccination. In contrast, the differences in the IgG1 titer were not so strongly pronounced, since the induction of IgG1 antibodies in all mouse groups turned out weaker than that of the IgG2a antibodies. Despite this, it is apparent that the subcutaneous immunization effected the weakest increase in IgG1. It could already be shown in the context of the first immunization study that the subcutaneous AdV-F$_{syn}$ vaccination induces an antibody titer which is many times higher for IgG2a than for IgG1, which speaks for a T$_H$1-mediated immune reaction. This result was also seen here in the second experiment with subcutaneous vaccination. In contrast, in intramuscular and intranasal immunization with AdV-F$_{syn}$, the IgG2a/IgG1 ratio was smaller. While still more IgG2a than IgG1 antibodies were formed following intramuscular vaccination, the proportion of IgG2a and IgG1 following intranasal immunization was quite balanced (FIG. 7). The T$_H$1-mediated path is thus most strongly activated in the immune reaction against RSV with subcutaneous immunization. But the ratio of T$_H$1 (IgG2a) and T$_H$2 (IgG1) is also balanced in intranasal vaccination, which speaks for a balanced T$_H$1/T$_H$2 response. Thus, according to the distribution of IgG antibody classes, no excess T$_H$2 response is generated via any of the three administration routes, which is significant for a vaccination against RSV.

Moreover, a further increase in titer for both IgG antibody classes was present from the serum sample following the first immunization to the serum sample following the second administration in all three mice groups immunized with AdV-F$_{syn}$, wherein the increase in titer was lowest with intranasal immunization and was highest with subcutaneous immunization (FIG. 7). One can thus establish that a boost with AdV-F$_{syn}$ vaccination induces a further antibody increase and thus makes sense for building up good immunity against RSV.

Figure 8:
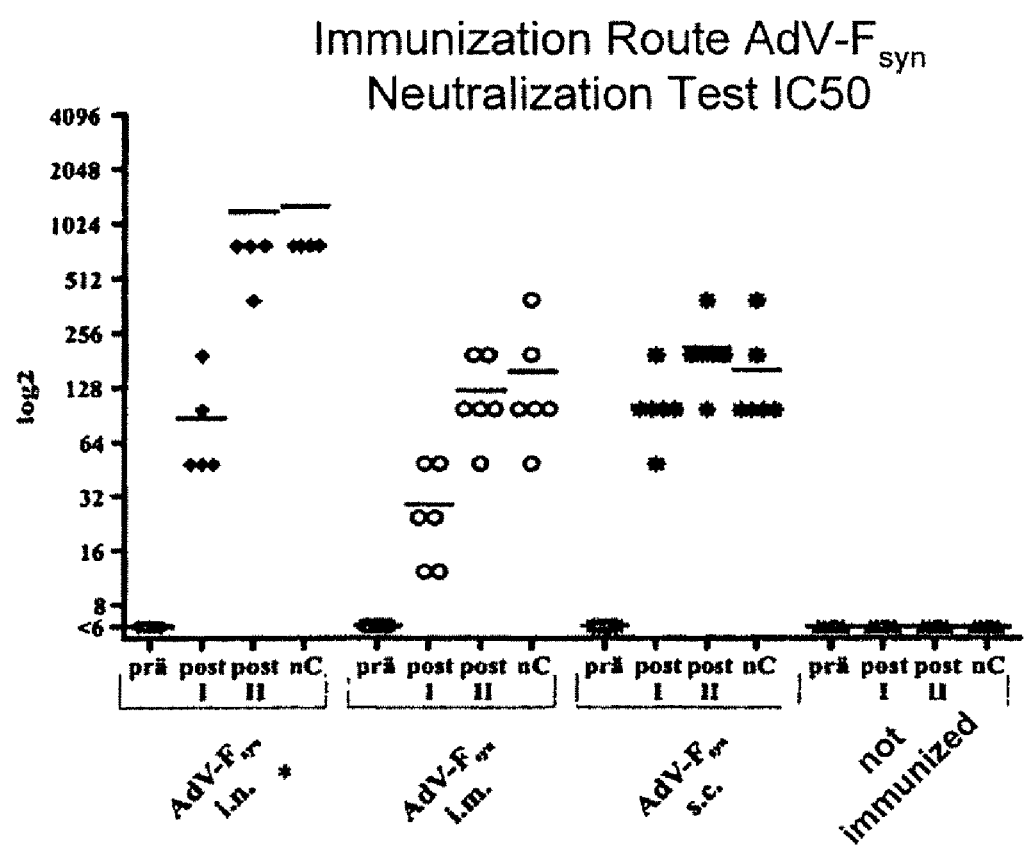
FIG. 8 shows the result of a neutralization test of mice, which were immunized by different administration paths with an adenoviral vector according to the invention, said adenoviral vector comprising a nucleic acid molecule coding for a codon-optimized RSV-F protein. The serum samples of the mice obtained before the first immunization (prä), after the first immunization (post I), after the second immunization (post II) and after the challenge on the day of death (nC) were serially diluted and then the dilution series was tested in the neutralization test for neutralizing antibodies against RSV. Each of the highest serum dilution at which the infection by RSV was inhibited by 50% (IC50) is shown. Each of the individual values of 5 (*) or 6 mice (black symbols) as well as the average value (bars) are shown.

It was also seen once again in the neutralization test that vaccination with Adv-F$_{syn}$ induces a very strong specific serum antibody response against RSV: while no neutralizing antibodies against RSV could be detected in any of the mice groups prior to the first immunization, and while this titer also did not increase in the non-immunized control group, a strong increase of RSV-specific neutralizing antibodies was observed in the three groups vaccinated with AdV-F$_{syn}$. As in the IgG ELISA and in the RSV qRT-PCR (lung homogenate), differences were also present here as dependent on the route of administration. For instance, the intranasal immunization led to the strongest increase of neutralizing activity, wherein the titer increased by a factor of approximately 200. Here, the increase in titer following intranasal immunization was 10-fold stronger than after intramuscular vaccination (here, an increase in titer by a factor of approximately 20 was observed) and 6-fold stronger than following subcutaneous vaccination (here, an increase in titer by a factor of approximately 35 was observed). It was thus shown that the immunization with AdV-$F_{syn}$ elicits a very good response of systemic neutralizing antibodies against RSV independent of the route of administration (intranasal, intramuscular, subcutaneous), wherein the intranasal route induces the strongest response (FIG. 8).

It was further observed here, as also already by ELISA, that the second immunization induces a further increase in antibodies. The neutralizing activity had increased significantly in the serum following the second immunization in comparison to the serum following the first immunization, most strongly in the intranasally immunized group (approximately 14-fold), and most weakly in the subcutaneously immunized group (approximately 2-fold) (FIG. 8).

In total, the result of the neutralization test showed stronger analogies to the qRT-PCR from the RNA isolates from the lung homogenate than to the ELISA. For instance, the induced titer of RSV-specific neutralizing antibodies corresponded to the reduction of RSV load in the lung, but not with the titer of the RSV-specific antibodies detected in the ELISA. This leads to the conclusion that the ELISA detects not only the RSV-specific neutralizing antibodies, but rather other non-neutralizing antibodies directed against RSV. Since the RSV-specific neutralizing antibodies participate essentially in the induction of protection against RSV, as is clear from the correlation between the titer of neutralizing antibodies and the reduction of the RSV load in the lung, one can better rely on the neutralization test than the ELISA in an evaluation of the protection following vaccination.

The clearly best vaccination result was achieved in the immunization study performed with the intranasal immunization, since, following intranasal immunization, on the one hand the highest titer of neutralizing antibodies was found with AdV-$F_{syn}$ and, on the other hand, the RSV load in the lung was most strongly (almost completely) reduced. The intranasal route is thus to be favored in prime-boost vaccination with AdV-$F_{syn}$.

Example 12

Subcutaneous Immunization with AdV-$F_{syn}$ in Different Doses (Dose Escalation)

In this experiment, the influence of the vaccine dose on the subcutaneous immunization with AdV-$F_{syn}$ is to be studied. To this end, four groups, each with 6 BALB/c mice, were each immunized subcutaneously with dosings of $2 \times 10^8$ to $2 \times 10^8$ GTU ($1 \times 10^7$ to $1 \times 10^{10}$ OPU) AdV-$F_{syn}$. A fifth group, also with 6 BALB/c mice was not immunized (negative control). The timeline for the vaccinations, blood removal and challenge was adopted from the first immunization study (see example 10).

On the day of killing (5 days following infection), the BALs and lung homogenates of the mice were obtained. Following isolation of viral RNA from the BAL and total RNA from the lung homogenate, quantitative RT-PCRs were performed in order to determine the RSV load in the RNA isolates and make a statement with regard to the protection of the animals following vaccination. In the RNA isolates from the BALs as well as the RNA isolates from the lung homogenates, the RSV load was very high in the non-immunized control group, wherein the detection of the RSV copies was again clearly more sensitive in the RNA isolates from the lung homogenates.

Figure 9:
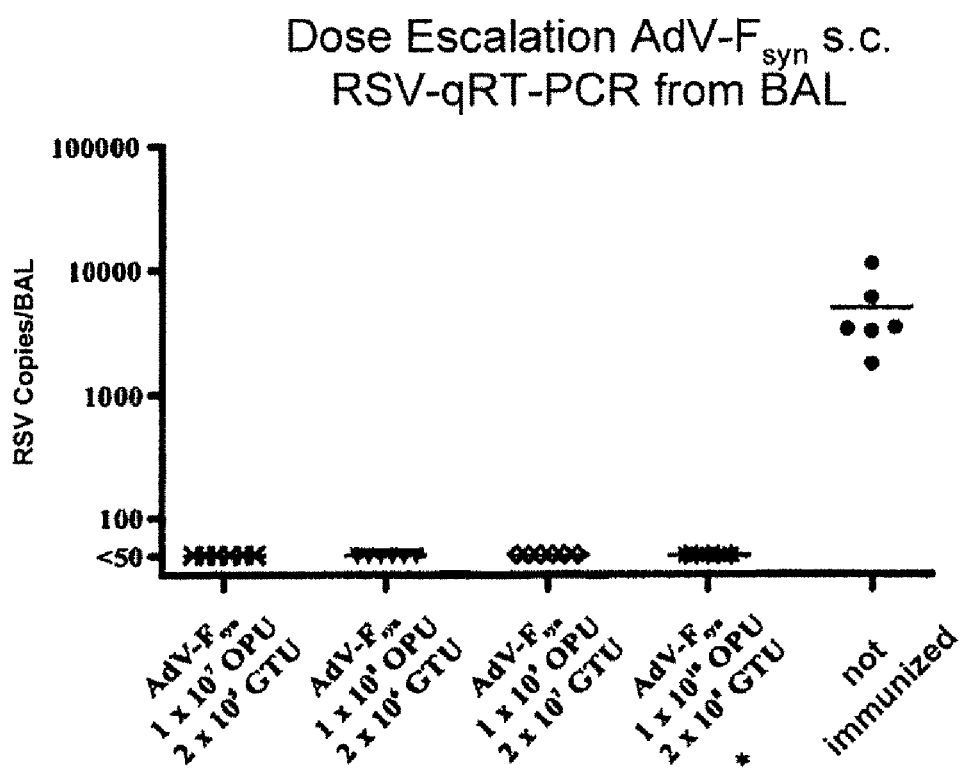
FIG. 9 shows the results of an RSV-qRT-PCR of RNA isolates from the bronchoalveolar lavage (BAL) of mice following subcutaneous immunization with an adenoviral vector according to the invention, said adenoviral vector comprising a nucleic acid molecule coding for a codon-optimized RSV-F protein (AdV-$F_{syn}$) in differing dosages (dose escalation). The RSV copy number according to qRT-PCR was standardized by RNA quantification and is depicted for the RNA isolates of the BALs recovered on the day of death. Each of the individual values of 5 (*) or 6 mice (black symbols) as well as the average value (bars) are shown.

All 4 immunized mice groups showed a good protection in qRT-PCR from the isolates from the BALs, since no RSV load was detectable in any single mouse (reduction by a factor of at least approximately 95-fold) (FIG. 9).

Figure 10:
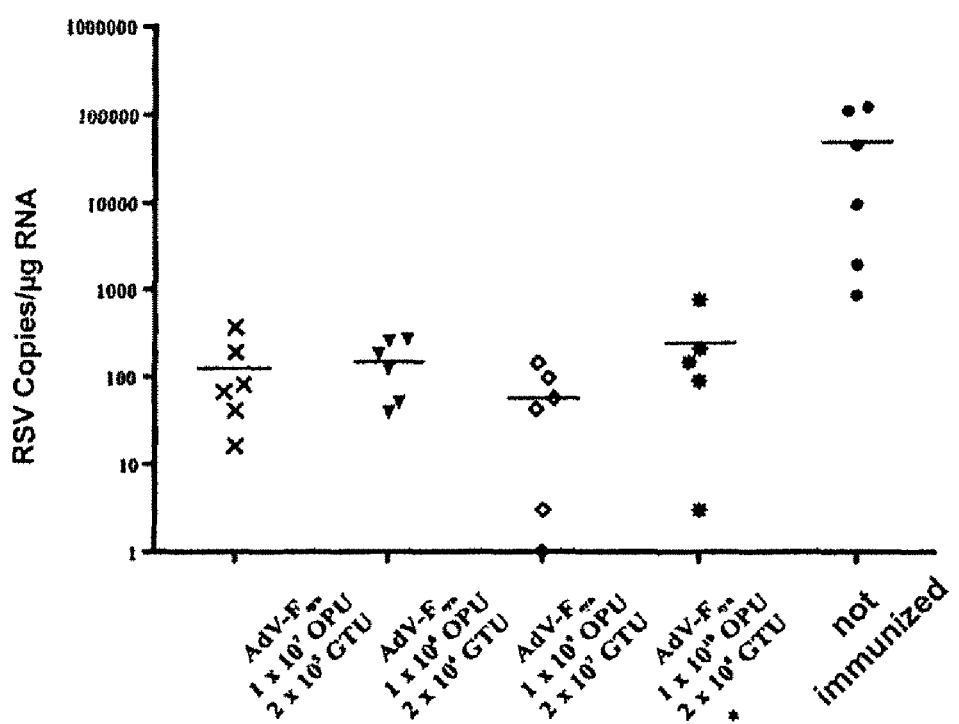
FIG. 10 shows the results of an RSV-qRT-PCR of RNA isolates from the lung homogenate of mice following subcutaneous immunization with an adenoviral vector according to the invention, said adenoviral vector comprising a nucleic acid molecule coding for a codon-optimized RSV-F protein (AdV-$F_{syn}$) in differing dosages (dose escalation). The results of the qRT-PCR of the RNA isolates of the lung homogenates recovered on the day of death are depicted. The RSV copy number according to qRT-PCR was standardized by RNA quantification and converted relative to the RNA content of the isolates. Each of the individual values of 5 (*) or 6 mice (black symbols) as well as the average value (bars) are shown.

In contrast, in the more sensitive qRT-PCR from the isolates of the lung homogenates, an RSV load was detectable even in the immunized mice, wherein the RSV copy number was comparable in all four immunization groups. For instance, an average reduction of the RSV load by a factor of approximately 340 from on average around 47,000 copies to on average around 140 copies was observed in all immunization groups (FIG. 10). All immunized mice were thus protected to the same extent irrespective of the vaccine dose, wherein a good, but not complete protection was observed. This means that the protection induced by a subcutaneous AdV-$F_{syn}$ vaccination is limited and cannot be further increased by raising the vaccine dose. On the one hand, a low vaccine dose is thus just as effective as a high vaccine dose in subcutaneous vaccination for building up a good protection. On the other hand, the subcutaneous route is not optimal in the AdV-$F_{syn}$ vaccination, since here (as opposed to the intranasal vaccination in the previous experiment) only a limited protection can be induced.

The sera of the mice obtained over the course of the immunization study were tested in IgG antibody ELISA and in the neutralization test for the induction of systemic RSV-specific antibodies.

Prior to the immunization, RSV-specific IgG or IgG2a antibodies were not detectable by ELISA in any mouse group. Nor did any increase in titer occur in the non-immunized control group over the course of the experiment. In contrast, a clear increase in RSV-specific titer in IgG1 as well as in IgG2 antibodies was observed in the four mouse groups vaccinated subcutaneously with AdV-$F_{syn}$. Here, this increase—as opposed to in RSV-qRT-PCR—was dependent on the dose of the vaccine. Only a minimal difference in the mouse groups was observed in the IgG1 antibodies since, as was also already shown in the immunization studies up to now, in principle only low IgG1 antibody titers are induced by subcutaneous vaccination, since the immune response proceeds in a $T_H1$ mediated manner. The increase in titer of the RSV-specific IgG1 antibodies in all four groups thus turned out to be equally weak. A slightly stronger increase could be induced by the boost only with very high vaccine dose. In contrast, with the IgG2a antibodies the four mouse groups showed, a clearly varying increase in titer irrespective of the vaccine dose, so that a direct dependence between vaccine dose and increase in titer exists here as well. For instance, the titer increased differently dependent on the dose not only after the first immunization but also after the second immunization. While following the first immunization the titer increased from one stage of the dosing to the next (from mouse group to mouse group) relatively linearly, in other words approximately by the same amount in each, an exponential dependence was observed after the boost, since the second immunization in low dose effected only a weak further increase in titer, but at high dose a strong further increase in titer. Subcutaneous immunization with AdV-$F_{syn}$ thus leads to a dose-dependent increase in the titer of RSV-specific antibodies, differently than in the RSV load corresponding to qRT-PCR.

Figure 11:
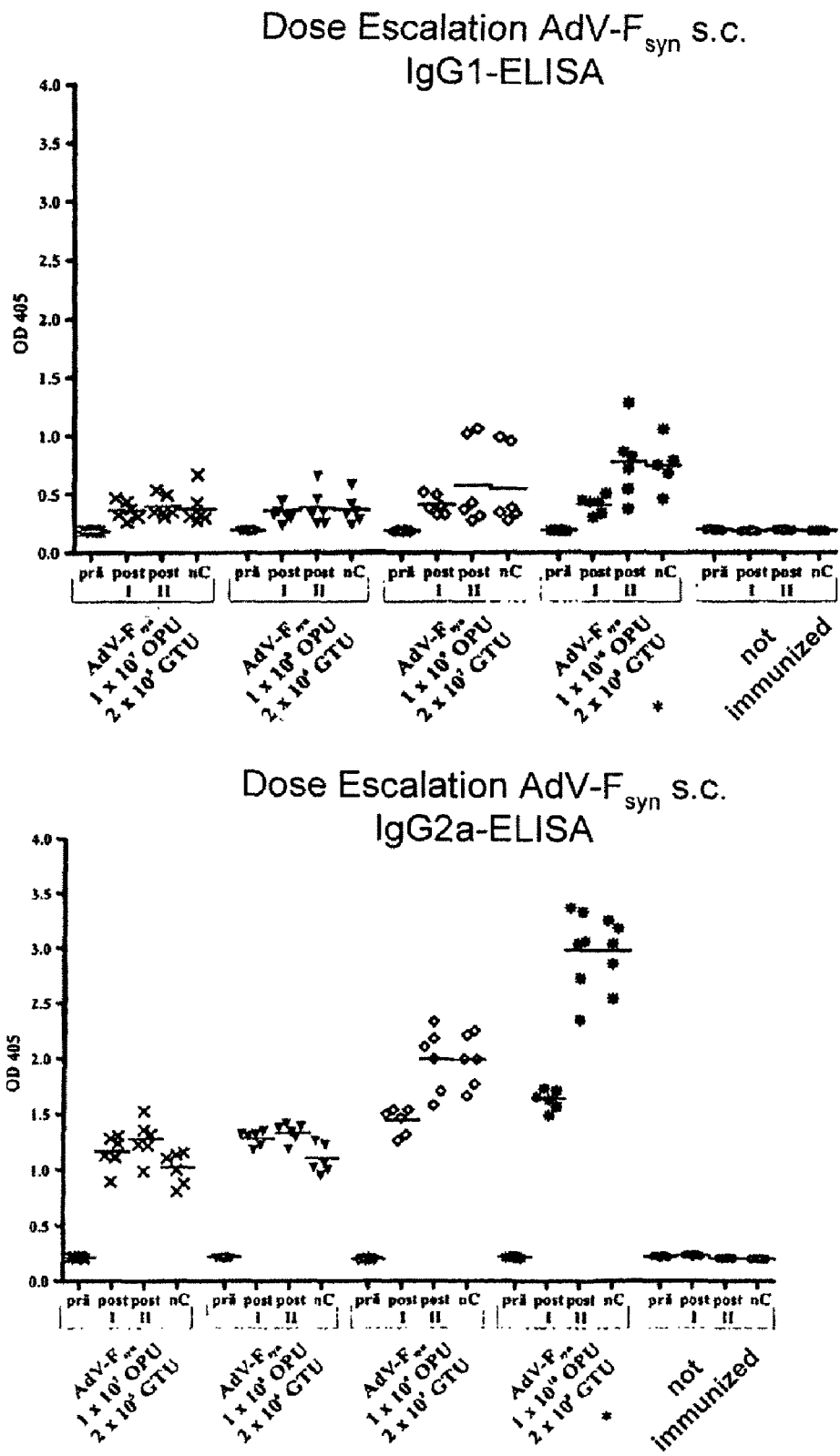
FIG. 11 shows the result of an IgG antibody ELISA from mice following subcutaneous immunization with an adenoviral vector according to the invention, said adenoviral vector comprising a nucleic acid molecule coding for a codon-optimized RSV-F protein (AdV-$F_{syn}$) in differing dosages (dose escalation). The serum samples of the mice obtained before the first immunization (prä), after the first immunization (post I), after the second immunization (post II) and after the challenge on the day of death (nC) were tested in the IgG antibody ELISA for RSV-specific IgG1- and IgG2a-antibodies. The intensity of the absorption at the wavelength 405 corresponds to the antibody titer in the blood of the mice. Each of the individual values of 5 (*) or 6 mice (black symbols) as well as the average value (bars) are shown.

While the second immunization at high dose led to a strong further increase in titer, hardly any further increase in titer was effected at low doses by the boost, so that—as far as the RSV-specific antibody titer corresponding to the ELISA is concerned—the boost only seems to make sense at the two highest doses (FIG. 11).

A neutralization test for RSV-specific neutralizing antibodies was also performed. Both before immunization and in the non-immunized control group, no titer was detectable. In contrast, neutralizing antibodies were formed following subcutaneous vaccination with AdV-F$_{syn}$. Here, in the neutralization test, another picture was observed than in the ELISA. Here, a clear dose dependence in the induction of neutralizing antibodies was already apparent after the first immunization, wherein the titer increased exponentially from dose stage to dose stage. For instance, the titer at the dose of 2×10$^5$ GTU (1×10$^7$ OPU) increased by a factor of approximately 2.6, at the dose of 2×10$^6$ GTU (1×10$^8$ OPU) by a factor of approximately 3.3; at the dose of 2×10$^7$ GTU (1×10$^9$ OPU) by a factor of approximately 21; at the dose of 2×10$^8$ GTU (1×10$^{10}$ OPU) by a factor of approximately 36.

Figure 12:
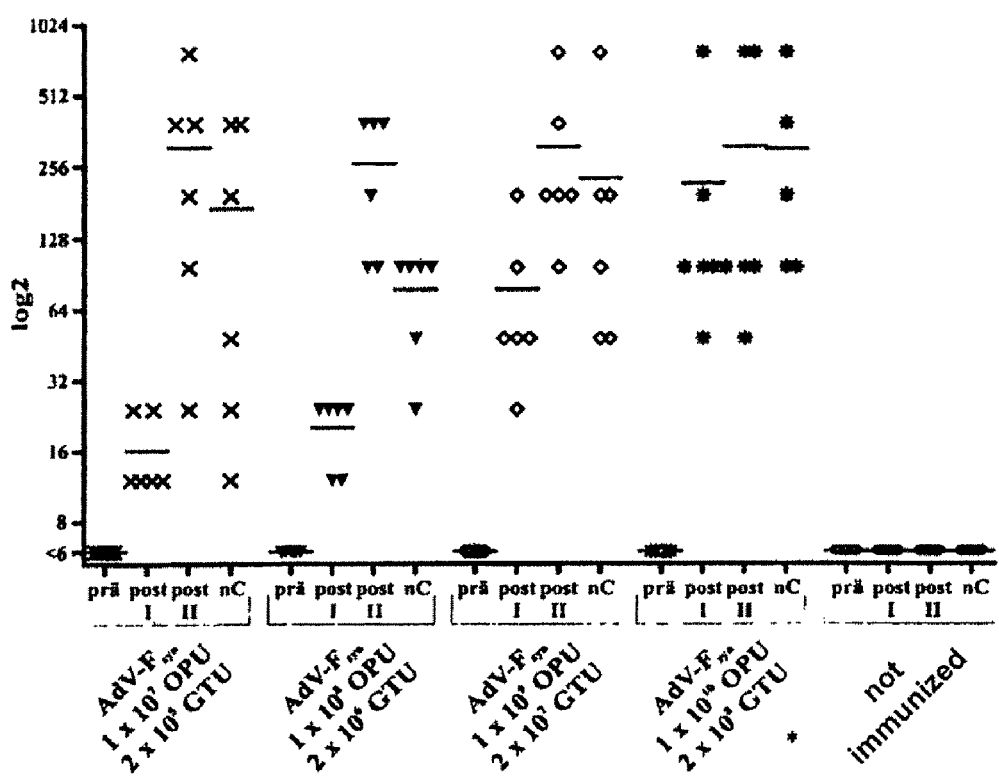
FIG. 12 shows the result of a neutralization test with mice after subcutaneous immunization with an adenoviral vector according to the invention, said adenoviral vector comprising a nucleic acid molecule (AdV-$F_{syn}$) coding for a codon-optimized RSV-F protein in differing dosages (dose escalation). The serum samples of the mice obtained before the first immunization (prä), after the first immunization (post I), after the second immunization (post II) and after the challenge on the day death (nC) were serially diluted and then the dilution series was tested in the neutralization test for neutralizing antibodies against RSV. Each highest serum dilution at which the infection by RSV was inhibited by 50% (IC50) with neutralizing antibodies is depicted. Each of the individual values of 5 (*) or 6 mice (black symbols) as well as the average value (bars) is shown.

Thus, while only a slight effect of increasing the dose was observed in the ELISA following the first immunization, the neutralizing antibodies were significantly more strongly induced by a high vaccine dose than by a low vaccine dose. In contrast, following the second immunization, a dose dependence could no longer be seen in the neutralization test (in contrast to the ELISA). In all immunized groups the antibody titer increased independently of the vaccine dose to a maximal value following the second immunization, wherein in each case the highest serum dilution at which the infection by RSV is inhibited by neutralizing antibodies by 50% (IC50) was on average 1:295. This means that in the two-fold subcutaneous immunization with AdV-F$_{syn}$, only one maximal titer of neutralizing antibodies can be built up, and this cannot be increased by a further increase in dose. This result is consistent with that from qRT-PCR of RNA isolates from the lung homogenate, since in this case as well a comparatively good protection (similar reduction of the RSV load) was observed in all immunized mice groups independent of the vaccine dose, once again showing that the antibodies detected in the neutralization test are essentially responsible for the protection from RSV infection. The result of the neutralization test thus shows, as does the RSV qRT-PCR, that a good protection from RSV infection with two-fold subcutaneous AdV-F$_{syn}$ immunization can also be achieved by a low vaccine dose and cannot be further increased by increasing this dose. As can be seen from the neutralization test, however, the boost seems to be absolutely necessary in order to induce, with a low vaccine dose, a protection which is just as good as with a high vaccine dose (FIG. 12).

Accordingly, in the two-fold subcutaneous immunization with AdV-F$_{syn}$ only a limited protection is achieved, since the maximal achieved value with regard to the reduction of RSV load in the lung and induced titer of neutralizing antibodies cannot be further increased, even by raising the dose. This result reinforces the conclusion, drawn from the previous immunization study, that the intranasal route is to be favored. Further, since following the second immunization the same maximal titer of neutralizing antibodies was achieved and the RSV load in the lung was reduced to the same extent in all mouse groups, it seems that in the subcutaneous immunization with AdV-F$_{syn}$, a lower dose of AdV-F$_{syn}$ is sufficient for the same vaccination success as long as a prime-boost strategy is chosen.

Example 13

Increase in Expression of RSV-F Protein in the Use of Codon-Optimized Expression Sequences Following incorporation (transfection) of the expression plasmids pFwt (expression plasmid with the wild-type sequence of the RSV-F protein), pIFwt (expression plasmid with the wild-type sequence of the RSV-F protein with an additional intron before the open reading frame), pFsyn (expression plasmid with the codon-optimized sequence of the RSV-F protein) and pIFsyn (expression plasmid with a codon-optimized sequence of the RSV-F protein with an additional intron before the open reading frame) in Hep2 cells, these were lysed 48 hours thereafter. The proteins of the cell lysate were separated by means of gel electrophoresis according to their size and subsequently transferred onto a nitrocellulose membrane.

Figure 14:
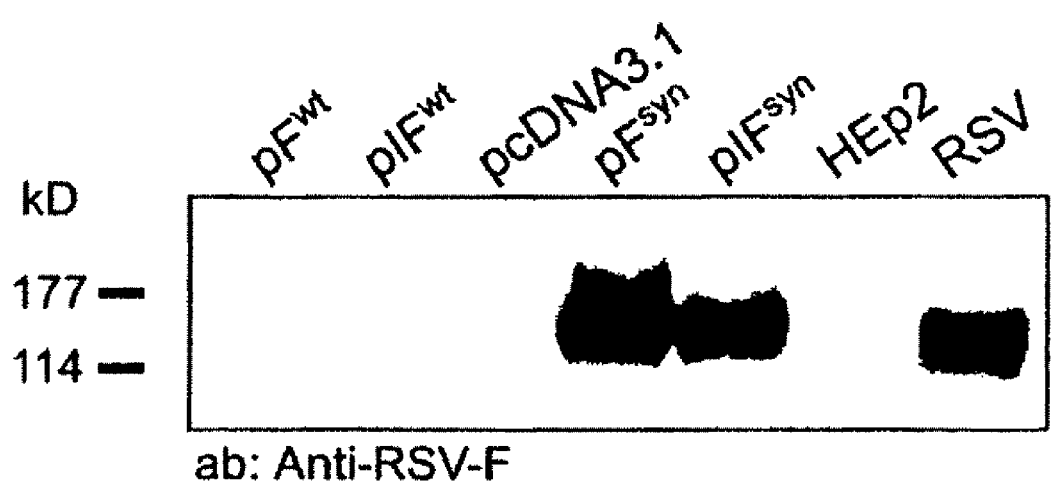
FIG. 14 shows expression differences of pFwt (expression plasmid with the wild-type sequence of the RSV-F protein), plFwt (expression plasmid with the wild-type sequence of the RSV-F protein with an additional intron before the open reading frame), pFsyn (expression plasmid with the codon-optimized sequence of the RSV-F protein) and plFsyn (expression plasmid with the codon-optimized sequence of the RSV-F protein with an additional intron before the open reading frame) after transfection in Hep2 cells, lysis of the cells 48 hours after transfection, separation of the proteins of the cell lysate by means of gel electrophoresis, transfer onto a nitrocellulose membrane and detection by means of a specific antibody (Ab: anti-RSV-F). pcDNA3.1: plasmid without foreign gene (empty plasmid); Hep2: cells without plasmid; RSV: cells infected with RSV (positive control); kD: molecular weight in kilodalton.

In the cell lysates, the amount of expressed RSV-F protein was determined (FIG. 14). A plasmid without a foreign gene (empty plasmid; pcDNA3.1), cells without plasmid (Hep2) and cells infected with RSV (positive control; RSV) served as controls. The results show that expression is only achievable by codon-optimization (comparison of pFwt or pIFwt to pFsyn or pIFsyn).

Figure 15:
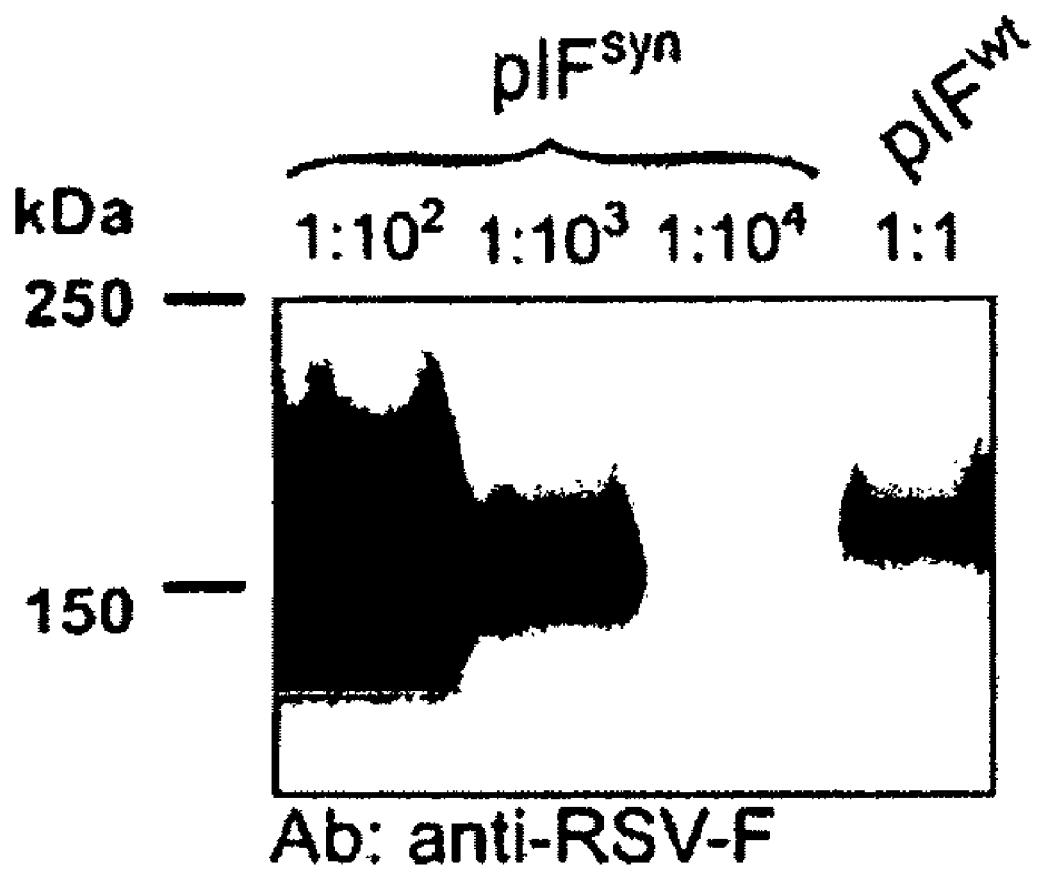

The expression of the codon-optimized construct (pIFsyn) was compared by serial dilution (1:10$^2$ to 1:10$^4$) of the cell lysate with the expression of the plasmid carrying the original sequence (pIFwt) in undiluted cell lysate (1:1) (FIG. 15). The amount of protein from RSV-F by expression of the codon-optimized construct in a dilution of 1000-fold (1:10$^3$) is still significantly greater than that by the plasmid with the original sequence. (kDa=molecular weight in kilodalton)

The results show that the codon-optimized nucleic acid sequence with the SEQ ID NO: 2 according to the invention increases the expression of the RSV-F protein in cells in an uncommonly strong manner (FIG. 14; FIG. 15). In contrast to the known increases in expression of generally 50- to a maximum of 100-fold, in the case of using the sequence according to the invention, an increase in the expression of RSV-F protein of over 1000-fold is observed. In contrast to other viral proteins, e.g. VSV-G protein, an amplification of expression of the RSV-F protein cannot be achieved simply by upstream placement of an intron.

The invention claimed is:

1. An isolated nucleic acid molecule comprising a nucleotide sequence which codes for an F-protein of the respiratory syncytial virus (RSV), wherein the nucleotide sequence comprises SEQ ID NO: 2.

2. A method of inducing an immunogenic response in a subject in need thereof, the method comprising administering to the subject a nucleic acid molecule according to claim 1.

3. A synthetic polypeptide coded by the nucleic acid molecule according to claim 1.

4. An isolated vector comprising the nucleic acid molecule according to claim 1.

5. The vector according to claim 4 wherein the vector is a viral vector or a plasmid vector.

6. The vector according to claim 5, wherein the viral vector is an adenoviral vector comprising (a) the nucleic acid molecule according to claim 3 and (b) a transcription and/or translation control sequence in functional linkage with the nucleic acid molecule.

7. An immunogenic composition comprising a nucleic acid molecule according to claim 1 and a pharmaceutically acceptable carrier.

8. An immunogenic composition comprising a polypeptide according to claim 3 and a pharmaceutically acceptable carrier.

9. An immunogenic composition comprising a vector according to claim 4 and a pharmaceutically acceptable carrier.

10. An immunogenic composition comprising a vector according to claim 5 and a pharmaceutically acceptable carrier.

11. An immunogenic composition comprising a vector according to claim 6 and a pharmaceutically acceptable carrier.

12. A method of inducing an immunogenic response in a subject in need thereof, the method comprising administering to the subject a polypeptide according to claim 3.

13. A method of inducing an immunogenic response in a subject in need thereof, the method comprising administering to the subject a vector according to claim 4.

14. A method of inducing an immunogenic response in a subject in need thereof, the method comprising administering to the subject a vector according to claim 5.

15. A method of inducing an immunogenic response in a subject in need thereof, the method comprising administering to the subject a vector according to claim 6.

16. A method of preparing an RSV-F protein, wherein the method comprises (a) transfecting a host cell with a nucleic acid molecule according to claim 1, and (b) expressing the nucleic acid molecule in the host cell.

* * * * *

SEQUENCE LISTING

<160> NUMBER OF SEQ ID NOS: 5

<210> SEQ ID NO 1
<211> LENGTH: 1725
<212> TYPE: DNA
<213> ORGANISM: respiratory syncytial virus

<400> SEQUENCE: 1
atggagttgc caatcctcaa agcaaatgca attaccacaa tcctcgctgc agtcacattt     60

```
tgctttgctt ctagtcaaaa catcactgaa gaattttatc aatcaacatg cagtgcagtt    120
agcaaaggct atcttagtgc tctaagaact ggttggtata ctagtgttat aactatagaa    180
ttaagtaata tcaaggaaaa taagtgtaat ggaacagatg ctaaggtaaa attgatgaaa    240
caagaattag ataaatataa aaatgctgta acagaattgc agttgctcat gcaaagcaca    300
ccagcagcaa acaatcgagc cagaagagaa ctaccaaggt ttatgaatta tacactcaac    360
aataccaaaa aaccaatgt aacattaagc aagaaaagga aagaagatt tcttggtttt    420 ttgttaggtg ttggatctgc aatcgccagt ggcattgctg tatctaaggt cctgcactta    480
gaaggagaag tgaacaagat caaaagtgct ctactatcca caacaaggc cgtagtcagc    540 ttatcaaatg gagttagtgt cttaaccagc aaagtgttag acctcaaaaa ctatatagat    600
aaacaattgt tacctattgt gaataagcaa agctgcagaa tatcaaatat agaaactgtg    660
atagagttcc aacaaagaa caacagacta ctagagatta ccagggaatt tagtgttaat    720
gtaggtgtaa ctacacctgt aagcacttac atgttaacta atagtgaatt attgtcatta    780
atcaatgata tgcctataac aaatgatcag aaaaagttaa tgtccaacaa tgttcaaata    840
gttagacagc aaagttactc tatcatgtcc ataataaaag aggaagtctt agcatatgta    900
gtacaattac cactatatgg tgtgatagat acaccttgtt ggaaattaca cacatcccct    960
ctatgtacaa ccaacacaaa agaagggtca aacatctgtt taacaagaac tgacagagga   1020
tggtactgtg acaatgcagg atcagtatct ttcttcccac aagctgaaac atgtaaagtt   1080
caatcgaatc gagtattttg tgacacaatg aacagtttaa cattaccaag tgaagtaaat   1140
ctctgcaatg ttgacatatt caatcccaaa tatgattgta aaattatgac ttcaaaaaca   1200
gatgtaagca gctccgttat cacatctcta ggagccattg tgtcatgcta tggcaaaact   1260
aaatgtacag catccaataa aaatcgtgga atcataaaga cattttctaa cgggtgtgat   1320
tatgtatcaa ataaggggt ggacactgtg tctgtaggta acacattata ttatgtaaat   1380
aagcaagaag gcaaaagtct ctatgtaaaa ggtgaaccaa taataaattt ctatgaccca   1440
ttagtattcc cctctgatga atttgatgca tcaatatctc aagtcaatga gaagattaac   1500
cagagtttag catttattcg taaatccgat gaattattac ataatgtaaa tgctggtaaa   1560
tcaaccacaa atatcatgat aactactata attatagtga ttatagtaat attgttatca   1620
ttaattgctg ttggactgct cctatactgt aaggccagaa gcacaccagt cacactaagc   1680
aaggatcaac tgagtggtat aaataatatt gcatttagta actaa               1725
```

<210> SEQ ID NO 2
<211> LENGTH: 1728
<212> TYPE: DNA
<213> ORGANISM: Artificial Sequence
<220> FEATURE:
<223> OTHER INFORMATION: Nucleotide sequence coding the F Protein of
      RSV, and optimized for the expression in human host cells

<400> SEQUENCE: 2

```
atggagctgc ctatcctgaa ggccaacgcc atcaccacaa ttctggccgc cgtgaccttc     60
tgttttgcca gcagccagaa catcaccgag gagttctacc agagcacctg tagcgccgtg    120
agcaagggct atctgagcgc cctgagaacc ggctggtaca ccagcgtgat caccatcgag    180
ctgagcaaca tcaaggagaa caagtgcaac ggcaccgacg ccaaggtgaa gctgatgaag    240
caggagctgg acaagtacaa gaacgccgtg accgaactgc agctgctgat gcagtctacc    300
cctgccgcca caacagagc cagacgggag ctgccccgt tcatgaacta cacccctgaac    360 aacaccaaga aaccaacgt gaccctgagc aagaagcgga agcggagatt cctgggcttt    420
```

```
ctgctgggag tgggctctgc catcgcctct ggcatcgccg tgtctaaggt gctgcacctg    480
gagggagagg tgaacaagat caagagcgcc ctgctgagca ccaataaggc cgtggtgagc    540
ctgagcaatg gcgtgagcgt gctgacaagc aaggtgctgg acctcaagaa ctacatcgac    600
aagcagctgc tgcccatcgt gaacaagcag agctgccgga tcagcaacat cgagaccgtg    660
atcgagttcc agcagaagaa caaccggctg ctggagatca ccagggagtt cagcgtgaat    720
gtgggcgtga ccacccctgt gagcacctac atgctgacca cagcgagct gctgagcctg    780 atcaacgaca tgcccatcac caacgaccag aagaagctga tgtccaacaa cgtgcagatc    840
gtgcggcagc agagctacag catcatgtcc atcatcaagg aggaggtgct ggcttacgtg    900
gtgcagctgc ctctgtacgg cgtgatcgac accccttgct ggaagctgca caccagccct    960
ctgtgcacca ccaataccaa ggagggcagc aacatctgcc tgaccaggac cgatagaggc   1020
tggtactgcg acaatgccgg cagcgtgagc ttctttccac aggccgagac ctgtaaggtg   1080
cagagcaacc gggtgttctg cgacaccatg aacagcctga ccctgccttc tgaggtgaac   1140
ctgtgcaacg tggacatctt caaccccaag tacgactgca gatcatgac cagcaagacc   1200 gacgtgagca gcagcgtgat tacaagcctg ggcgccatcg tgagctgtta cggcaagacc   1260
aagtgcaccg ccagcaacaa gaaccgcggc atcatcaaga ccttcagcaa cggctgcgac   1320
tacgtgagca caagggcgt ggatacagtg agcgtgggca cacccctgta ctacgtcaac   1380
aagcaggagg gcaagagcct gtacgtgaag ggcgagccca tcatcaactt ctacgacccc   1440
ctggtgttcc ctagcgacga gttcgatgcc agcatcagcc aggtgaacga gaagatcaac   1500
cagagcctgg ccttcatcag gaagagcgac gagctgctgc acaatgtgaa cgccggcaag   1560
agcaccacca acatcatgat caccaccatc atcatcgtga tcatcgtcat cctgctgtcc   1620
ctgattgctg tgggcctgct gctgtactgt aaggccagaa gcaccccgt gaccctgtct   1680 aaggatcagc tgagcggcat caacaacatc gccttctcca actgataa              1728
```

<210> SEQ ID NO 3
<211> LENGTH: 574
<212> TYPE: PRT
<213> ORGANISM: respiratory syncytial virus

<400> SEQUENCE: 3

Met Glu Leu Pro Ile Leu Lys Ala Asn Ala Ile Thr Thr Ile Leu Ala
1               5                   10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Ala Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Met Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Lys Lys Thr Asn Val Thr
        115                 120                 125

Leu Ser Lys Lys Arg Lys Arg Arg Phe Leu Gly Phe Leu Leu Gly Val
    130                 135                 140

```
Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
            165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Arg Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Val Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
            565                 570
```

```
<210> SEQ ID NO 4
<211> LENGTH: 37
<212> TYPE: DNA
<213> ORGANISM: Artificial Sequence
<220> FEATURE:
<223> OTHER INFORMATION: Oligonucleotide primer (sense)

<400> SEQUENCE: 4
gatccaagct tccaccatgg agttgccaat cctcaaa                              37

<210> SEQ ID NO 5
<211> LENGTH: 41
<212> TYPE: DNA
<213> ORGANISM: Artificial Sequence
<220> FEATURE:
<223> OTHER INFORMATION: Oligonucleotide primer (antisense)

<400> SEQUENCE: 5
tcgacctcga gttagttact aaatgcaata ttatttatac c                         41
```